(12) United States Patent
Minassian et al.

(10) Patent No.: US 11,992,684 B2
(45) Date of Patent: May 28, 2024

(54) SYSTEM FOR PLANNING AND/OR PROVIDING NEUROMODULATION

(71) Applicants: ECOLE POLYTECHNI UE FEDERALE DE LAUSANNE (EPFL), Lausanne (CH); ONWARD Medical N.V., Eindhoven (NL)

(72) Inventors: Karen Minassian, Vienna (AT); Fabien Wagner, Lausanne (CH); Marco Capogrosso, Lausanne (CH); Gregoire Courtine, Lausanne (CH); Robin Brouns, Eindhoven (NL); Jurriaan Bakker, Eindhoven (NL); Andre Kleibeuker, Eindhoven (NL); Bert Bakker, Eindhoven (NL); Vincent Delattre, Eindhoven (NL)

(73) Assignees: ECOLE POLYTECHNIQUE FEDERALE DE LAUSANNE (EPFL), Lausanne (CH); ONWARD MEDICAL N.V., Eindhoven (NL)

( * ) Notice: Subject to any disclaimer, the term of this patent is extended or adjusted under 35 U.S.C. 154(b) by 780 days.

(21) Appl. No.: 16/769,213

(22) PCT Filed: Nov. 29, 2018

(86) PCT No.: PCT/EP2018/082942
§ 371 (c)(1),
(2) Date: Jun. 2, 2020

(87) PCT Pub. No.: WO2019/110400
PCT Pub. Date: Jun. 13, 2019

(65) Prior Publication Data
US 2021/0170177 A1 Jun. 10, 2021

(30) Foreign Application Priority Data
Dec. 5, 2017 (EP) ..................... 17205360

(51) Int. Cl.
*A61N 1/36* (2006.01)
*A61N 1/05* (2006.01)
(Continued)

(52) U.S. Cl.
CPC ....... *A61N 1/36135* (2013.01); *A61N 1/0551* (2013.01); *A61N 1/36003* (2013.01);
(Continued)

(58) Field of Classification Search
CPC ............ A61N 1/36135; A61N 1/36062; A61N 1/0551; A61N 1/36003; G16H 20/40; G16H 10/60; G16H 50/20; G16H 40/63
See application file for complete search history.

(56) References Cited

U.S. PATENT DOCUMENTS

| | | |
|---|---|---|
| 3,543,761 A | 12/1970 | Bradley |
| 3,650,277 A | 3/1972 | Sjostrand et al. |

(Continued)

FOREIGN PATENT DOCUMENTS

| | | |
|---|---|---|
| AU | 2012204526 B2 | 9/2016 |
| CA | 2856202 A1 | 5/2013 |

(Continued)

OTHER PUBLICATIONS

Bizzi, E. et al., "Modular Organization of Motor Behavior," Trends in Neurosciences, vol. 18, No. 10, Oct. 1995, 8 pages.
(Continued)

*Primary Examiner* — Ahmed M Farah
*Assistant Examiner* — Naveed R. Kolia
(74) *Attorney, Agent, or Firm* — McCoy Russell LLP

(57) ABSTRACT

The present invention relates to systems and methods for planning and/or providing neuromodulation One example system includes
a stimulation related basic data storage module for storing stimulation related basic data,
(Continued)

a stimulation related response data storage module for storing the stimulation related response data, a transfer module configured such that the stimulation related basic data are linked with and/or translated into the response data and/or artificial response data created by the transfer module, wherein the data generated by the transfer module are transfer data, the transfer data comprising link data and/or translation data and/or artificial response data, mapping module configured and arranged such that based on the stimulation related basic data and stimulation related response data and the transfer data a digital characteristic map is generated, and an analysis module configured and arranged such that the digital characteristic map is analyzed automatically.

12 Claims, 10 Drawing Sheets

(51) Int. Cl.
*G16H 10/60* (2018.01)
*G16H 20/40* (2018.01)
*G16H 40/63* (2018.01)
*G16H 50/20* (2018.01)

(52) U.S. Cl.
CPC ......... *A61N 1/36062* (2017.08); *G16H 10/60* (2018.01); *G16H 20/40* (2018.01); *G16H 40/63* (2018.01); *G16H 50/20* (2018.01)

(56) References Cited

U.S. PATENT DOCUMENTS

| | | |
|---|---|---|
| 3,662,758 A | 5/1972 | Glover |
| 3,724,467 A | 4/1973 | Avery et al. |
| 4,044,774 A | 8/1977 | Corbin et al. |
| 4,102,344 A | 7/1978 | Conway et al. |
| 4,141,365 A | 2/1979 | Fischell et al. |
| 4,285,347 A | 8/1981 | Hess |
| 4,340,063 A | 7/1982 | Maurer |
| 4,379,462 A | 4/1983 | Borkan et al. |
| 4,398,537 A | 8/1983 | Holmbo |
| 4,414,986 A | 11/1983 | Dickhudt et al. |
| 4,538,624 A | 9/1985 | Tarjan |
| 4,549,556 A | 10/1985 | Tarjan et al. |
| 4,559,948 A | 12/1985 | Liss |
| 4,569,352 A | 2/1986 | Petrofsky et al. |
| 4,573,481 A | 3/1986 | Bullara |
| 4,724,842 A | 2/1988 | Charters |
| 4,800,898 A | 1/1989 | Hess et al. |
| 4,934,368 A | 6/1990 | Lynch |
| 4,969,452 A | 11/1990 | Petrofsky et al. |
| 5,002,053 A | 3/1991 | Garcia-Rill et al. |
| 5,031,618 A | 7/1991 | Mullett |
| 5,066,272 A | 11/1991 | Eaton et al. |
| 5,081,989 A | 1/1992 | Graupe et al. |
| 5,121,754 A | 6/1992 | Mullett |
| 5,344,439 A | 9/1994 | Otten |
| 5,354,320 A | 10/1994 | Schaldach et al. |
| 5,366,813 A | 11/1994 | Berlin |
| 5,374,285 A | 12/1994 | Vaiani et al. |
| 5,417,719 A | 5/1995 | Hull et al. |
| 5,476,441 A | 12/1995 | Durfee et al. |
| 5,562,718 A | 10/1996 | Palermo |
| 5,643,330 A | 7/1997 | Holsheimer et al. |
| 5,733,322 A | 3/1998 | Starkebaum |
| 5,983,141 A | 11/1999 | Sluijter et al. |
| 6,058,331 A | 5/2000 | King |
| 6,066,163 A | 5/2000 | John |
| 6,104,957 A | 8/2000 | Alo et al. |
| 6,122,548 A | 9/2000 | Starkebaum et al. |
| 6,308,103 B1 | 10/2001 | Gielen |
| 6,319,241 B1 | 11/2001 | King et al. |
| 6,463,327 B1 | 10/2002 | Lurie et al. |
| 6,470,213 B1 | 10/2002 | Alley |
| 6,500,110 B1 | 12/2002 | Davey et al. |
| 6,503,231 B1 | 1/2003 | Prausnitz et al. |
| 6,505,074 B2 | 1/2003 | Boveja et al. |
| 6,516,227 B1 | 2/2003 | Meadows et al. |
| 6,551,849 B1 | 4/2003 | Kenney |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,748,276 B1 | 6/2004 | Daignault, Jr. et al. |
| 6,819,956 B2 | 11/2004 | DiLorenzo |
| 6,839,594 B2 | 1/2005 | Cohen et al. |
| 6,862,479 B1 | 3/2005 | Whitehurst et al. |
| 6,871,099 B1 | 3/2005 | Whitehurst et al. |
| 6,878,112 B2 | 4/2005 | Linberg et al. |
| 6,892,098 B2 | 5/2005 | Ayal et al. |
| 6,895,280 B2 | 5/2005 | Meadows et al. |
| 6,895,283 B2 | 5/2005 | Erickson et al. |
| 6,937,891 B2 | 8/2005 | Leinders et al. |
| 6,950,706 B2 | 9/2005 | Rodriguez et al. |
| 6,975,907 B2 | 12/2005 | Zanakis et al. |
| 6,988,006 B2 | 1/2006 | King et al. |
| 6,999,820 B2 | 2/2006 | Jordan |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,110,820 B2 | 9/2006 | Tcheng et al. |
| 7,127,287 B2 | 10/2006 | Duncan et al. |
| 7,127,296 B2 | 10/2006 | Bradley |
| 7,127,297 B2 | 10/2006 | Law et al. |
| 7,149,773 B2 | 12/2006 | Haller et al. |
| 7,153,242 B2 | 12/2006 | Goffer |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Campen et al. |
| 7,239,920 B1 | 7/2007 | Thacker et al. |
| 7,251,529 B2 | 7/2007 | Greenwood-Van Meerveld |
| 7,252,090 B2 | 8/2007 | Goetz |
| 7,313,440 B2 | 12/2007 | Miesel |
| 7,324,853 B2 | 1/2008 | Ayal et al. |
| 7,330,760 B2 | 2/2008 | Heruth et al. |
| 7,337,005 B2 | 2/2008 | Kim et al. |
| 7,337,006 B2 | 2/2008 | Kim et al. |
| 7,340,298 B1 | 3/2008 | Barbut |
| 7,377,006 B2 | 5/2008 | Genoa et al. |
| 7,381,192 B2 | 6/2008 | Brodard et al. |
| 7,415,309 B2 | 8/2008 | McIntyre |
| 7,463,927 B1 | 12/2008 | Chaouat |
| 7,463,928 B2 | 12/2008 | Lee et al. |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt et al. |
| 7,536,226 B2 | 5/2009 | Williams et al. |
| 7,544,185 B2 | 6/2009 | Bengtsson |
| 7,584,000 B2 | 9/2009 | Erickson |
| 7,590,454 B2 | 9/2009 | Garabedian et al. |
| 7,603,178 B2 | 10/2009 | North et al. |
| 7,620,502 B2 | 11/2009 | Selifonov et al. |
| 7,628,750 B2 | 12/2009 | Cohen et al. |
| 7,647,115 B2 | 1/2010 | Levin et al. |
| 7,660,636 B2 | 2/2010 | Castel et al. |
| 7,697,995 B2 | 4/2010 | Cross, Jr. et al. |
| 7,725,193 B1 | 5/2010 | Chu |
| 7,729,781 B2 | 6/2010 | Swoyer et al. |
| 7,734,340 B2 | 6/2010 | De Ridder |
| 7,734,351 B2 | 6/2010 | Testerman et al. |
| 7,742,037 B2 | 6/2010 | Sako et al. |
| 7,769,463 B2 | 8/2010 | Katsnelson |
| 7,797,057 B2 | 9/2010 | Harris |
| 7,801,601 B2 | 9/2010 | Maschino et al. |
| 7,813,803 B2 | 10/2010 | Heruth et al. |

(56) References Cited

U.S. PATENT DOCUMENTS

| | | |
|---|---|---|
| 7,813,809 B2 | 10/2010 | Strother et al. |
| 7,856,264 B2 | 12/2010 | Firlik et al. |
| 7,877,146 B2 | 1/2011 | Rezai et al. |
| 7,890,182 B2 | 2/2011 | Parramon et al. |
| 7,949,395 B2 | 5/2011 | Kuzma |
| 7,949,403 B2 | 5/2011 | Palermo et al. |
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,108,051 B2 | 1/2012 | Cross, Jr. et al. |
| 8,108,052 B2 | 1/2012 | Boling |
| 8,131,358 B2 | 3/2012 | Moffitt et al. |
| 8,135,473 B2 | 3/2012 | Miesel et al. |
| 8,155,750 B2 | 4/2012 | Jaax et al. |
| 8,168,481 B2 | 5/2012 | Hanaoka et al. |
| 8,170,660 B2 | 5/2012 | Dacey, Jr. et al. |
| 8,190,262 B2 | 5/2012 | Gerber et al. |
| 8,195,304 B2 | 6/2012 | Strother et al. |
| 8,214,048 B1 | 7/2012 | Whitehurst et al. |
| 8,229,565 B2 | 7/2012 | Kim et al. |
| 8,239,038 B2 | 8/2012 | Wolf |
| 8,260,436 B2 | 9/2012 | Gerber et al. |
| 8,271,099 B1 | 9/2012 | Swanson et al. |
| 8,295,936 B2 | 10/2012 | Wahlstrand et al. |
| 8,311,644 B2 | 11/2012 | Moffitt et al. |
| 8,326,569 B2 | 12/2012 | Lee et al. |
| 8,332,029 B2 | 12/2012 | Glukhovsky et al. |
| 8,332,047 B2 | 12/2012 | Libbus et al. |
| 8,346,366 B2 | 1/2013 | Arle et al. |
| 8,352,036 B2 | 1/2013 | DiMarco et al. |
| 8,355,791 B2 | 1/2013 | Moffitt |
| 8,355,797 B2 | 1/2013 | Caparso et al. |
| 8,364,273 B2 | 1/2013 | De Ridder |
| 8,369,961 B2 | 2/2013 | Christman et al. |
| 8,374,696 B2 | 2/2013 | Sanchez et al. |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishnamurthy et al. |
| 8,543,200 B2 | 9/2013 | Lane et al. |
| 8,588,884 B2 | 11/2013 | Hegde et al. |
| 8,626,300 B2 | 1/2014 | Demarais et al. |
| 8,700,145 B2 | 4/2014 | Kilgard et al. |
| 8,712,546 B2 | 4/2014 | Kim et al. |
| 8,740,825 B2 | 6/2014 | Ehrenreich et al. |
| 8,750,957 B2 | 6/2014 | Tang et al. |
| 8,768,481 B2 | 7/2014 | Lane |
| 8,805,542 B2 | 8/2014 | Tai et al. |
| 9,072,891 B1 | 7/2015 | Rao |
| 9,079,039 B2 | 7/2015 | Carlson et al. |
| 9,101,769 B2 | 8/2015 | Edgerton et al. |
| 9,205,259 B2 | 12/2015 | Kim et al. |
| 9,205,260 B2 | 12/2015 | Kim et al. |
| 9,205,261 B2 | 12/2015 | Kim et al. |
| 9,248,291 B2 | 2/2016 | Mashiach |
| 9,272,139 B2 | 3/2016 | Hamilton et al. |
| 9,272,143 B2 | 3/2016 | Libbus et al. |
| 9,283,391 B2 | 3/2016 | Ahmed |
| 9,314,630 B2 | 4/2016 | Levin et al. |
| 9,393,409 B2 | 7/2016 | Edgerton et al. |
| 9,409,023 B2 | 8/2016 | Burdick et al. |
| 9,415,218 B2 | 8/2016 | Edgerton et al. |
| 9,421,365 B2 | 8/2016 | Sumners et al. |
| 9,597,517 B2 | 3/2017 | Moffitt |
| 9,610,442 B2 | 4/2017 | Yoo et al. |
| 9,802,052 B2 | 10/2017 | Marnfeldt |
| 9,895,545 B2 | 2/2018 | Rao et al. |
| 9,993,642 B2 | 6/2018 | Gerasimenko et al. |
| 10,092,750 B2 | 10/2018 | Edgerton et al. |
| 10,124,166 B2 | 11/2018 | Edgerton et al. |
| 10,137,299 B2 | 11/2018 | Lu et al. |
| 10,449,371 B2 | 10/2019 | Serrano Carmona |
| 10,751,533 B2 | 8/2020 | Edgerton et al. |
| 10,773,074 B2 | 9/2020 | Liu et al. |
| 10,806,927 B2 | 10/2020 | Edgerton et al. |
| 10,806,935 B2 | 10/2020 | Rao et al. |
| 11,097,122 B2 | 8/2021 | Lu |
| 11,123,312 B2 | 9/2021 | Lu et al. |
| 2001/0016266 A1 | 8/2001 | Okazaki et al. |
| 2001/0032992 A1 | 10/2001 | Wendt |
| 2002/0042814 A1 | 4/2002 | Fukasawa et al. |
| 2002/0052539 A1 | 5/2002 | Haller et al. |
| 2002/0083240 A1 | 6/2002 | Hoese et al. |
| 2002/0111661 A1 | 8/2002 | Cross et al. |
| 2002/0115945 A1 | 8/2002 | Herman et al. |
| 2002/0188332 A1 | 12/2002 | Lurie et al. |
| 2002/0193843 A1 | 12/2002 | Hill et al. |
| 2003/0032992 A1 | 2/2003 | Thacker et al. |
| 2003/0078633 A1 | 4/2003 | Firlik et al. |
| 2003/0093021 A1 | 5/2003 | Goffer |
| 2003/0100933 A1 | 5/2003 | Ayal et al. |
| 2003/0114894 A1 | 6/2003 | Dar et al. |
| 2003/0158583 A1 | 8/2003 | Burnett et al. |
| 2003/0220679 A1 | 11/2003 | Han |
| 2003/0233137 A1 | 12/2003 | Paul, Jr. |
| 2004/0039425 A1 | 2/2004 | Greenwood-Van Meerveld |
| 2004/0044380 A1 | 3/2004 | Bruninga et al. |
| 2004/0111118 A1 | 6/2004 | Hill et al. |
| 2004/0111126 A1 | 6/2004 | Tanagho et al. |
| 2004/0122483 A1 | 6/2004 | Nathan et al. |
| 2004/0127954 A1 | 7/2004 | McDonald, III |
| 2004/0133248 A1 | 7/2004 | Frei et al. |
| 2004/0138518 A1 | 7/2004 | Rise et al. |
| 2004/0172027 A1 | 9/2004 | Speitling et al. |
| 2004/0172097 A1 | 9/2004 | Brodard et al. |
| 2004/0181263 A1 | 9/2004 | Balzer et al. |
| 2004/0267320 A1 | 12/2004 | Taylor et al. |
| 2005/0004622 A1 | 1/2005 | Cullen et al. |
| 2005/0061315 A1 | 3/2005 | Lee et al. |
| 2005/0070982 A1 | 3/2005 | Heruth et al. |
| 2005/0075669 A1 | 4/2005 | King |
| 2005/0075678 A1 | 4/2005 | Faul |
| 2005/0090756 A1 | 4/2005 | Wolf et al. |
| 2005/0101827 A1 | 5/2005 | Delisle |
| 2005/0102007 A1 | 5/2005 | Ayal et al. |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0209655 A1 | 9/2005 | Bradley et al. |
| 2005/0231186 A1 | 10/2005 | Saavedra Barrera et al. |
| 2005/0246004 A1 | 11/2005 | Cameron et al. |
| 2005/0277999 A1 | 12/2005 | Strother et al. |
| 2005/0278000 A1 | 12/2005 | Strother et al. |
| 2006/0003090 A1 | 1/2006 | Rodger et al. |
| 2006/0015153 A1 | 1/2006 | Gliner et al. |
| 2006/0018360 A1 | 1/2006 | Tai et al. |
| 2006/0041225 A1 | 2/2006 | Wallace et al. |
| 2006/0041295 A1 | 2/2006 | Osypka |
| 2006/0089696 A1 | 4/2006 | Olsen et al. |
| 2006/0100671 A1 | 5/2006 | Ridder |
| 2006/0111754 A1 | 5/2006 | Rezai et al. |
| 2006/0122678 A1 | 6/2006 | Olsen et al. |
| 2006/0142337 A1 | 6/2006 | Ikeura et al. |
| 2006/0142816 A1 | 6/2006 | Fruitman et al. |
| 2006/0142822 A1 | 6/2006 | Tulgar |
| 2006/0149333 A1 | 7/2006 | Tanagho et al. |
| 2006/0149337 A1 | 7/2006 | John |
| 2006/0189839 A1 | 8/2006 | Laniado et al. |
| 2006/0195153 A1 | 8/2006 | DiUbaldi et al. |
| 2006/0239482 A1 | 10/2006 | Hatoum |
| 2006/0241356 A1 | 10/2006 | Flaherty |
| 2006/0282127 A1 | 12/2006 | Zealear |
| 2007/0004567 A1 | 1/2007 | Shetty et al. |
| 2007/0016097 A1 | 1/2007 | Farquhar et al. |
| 2007/0016266 A1 | 1/2007 | Paul, Jr. |
| 2007/0016329 A1 | 1/2007 | Herr et al. |
| 2007/0021513 A1 | 1/2007 | Agee et al. |
| 2007/0027495 A1 | 2/2007 | Gerber |
| 2007/0047852 A1 | 3/2007 | Sharp et al. |
| 2007/0049814 A1 | 3/2007 | Muccio |
| 2007/0055337 A1 | 3/2007 | Tanrisever |
| 2007/0060954 A1 | 3/2007 | Cameron et al. |
| 2007/0060980 A1 | 3/2007 | Strother et al. |

(56) References Cited

U.S. PATENT DOCUMENTS

| | | |
|---|---|---|
| 2007/0067003 A1 | 3/2007 | Sanchez et al. |
| 2007/0073357 A1 | 3/2007 | Rooney et al. |
| 2007/0083240 A1 | 4/2007 | Peterson et al. |
| 2007/0100389 A1 | 5/2007 | Jaax et al. |
| 2007/0121702 A1 | 5/2007 | LaGuardia et al. |
| 2007/0121709 A1 | 5/2007 | Ittogi |
| 2007/0142874 A1 | 6/2007 | John |
| 2007/0150023 A1 | 6/2007 | Ignagni et al. |
| 2007/0156172 A1 | 7/2007 | Alvarado |
| 2007/0156179 A1 | 7/2007 | S.E. |
| 2007/0156200 A1 | 7/2007 | Kornet et al. |
| 2007/0168008 A1 | 7/2007 | Olsen |
| 2007/0179534 A1 | 8/2007 | Firlik et al. |
| 2007/0179579 A1 | 8/2007 | Feler et al. |
| 2007/0191709 A1 | 8/2007 | Swanson |
| 2007/0208381 A1 | 9/2007 | Hill et al. |
| 2007/0233204 A1 | 10/2007 | Lima et al. |
| 2007/0255372 A1 | 11/2007 | Metzler et al. |
| 2007/0265621 A1 | 11/2007 | Matthis et al. |
| 2007/0265679 A1 | 11/2007 | Bradley et al. |
| 2007/0265691 A1 | 11/2007 | Swanson |
| 2007/0276449 A1 | 11/2007 | Gunter et al. |
| 2007/0276450 A1 | 11/2007 | Meadows et al. |
| 2007/0293910 A1 | 12/2007 | Strother et al. |
| 2008/0002227 A1 | 1/2008 | Tsujimoto |
| 2008/0004674 A1 | 1/2008 | King et al. |
| 2008/0009927 A1 | 1/2008 | Vilims |
| 2008/0021513 A1 | 1/2008 | Thacker et al. |
| 2008/0027346 A1 | 1/2008 | Litt et al. |
| 2008/0046049 A1 | 2/2008 | Skubitz et al. |
| 2008/0051851 A1 | 2/2008 | Lin |
| 2008/0071325 A1 | 3/2008 | Bradley |
| 2008/0077192 A1 | 3/2008 | Harry et al. |
| 2008/0103579 A1 | 5/2008 | Gerber |
| 2008/0105185 A1 | 5/2008 | Kuhlman |
| 2008/0140152 A1 | 6/2008 | Imran et al. |
| 2008/0140162 A1 | 6/2008 | Goetz et al. |
| 2008/0140169 A1 | 6/2008 | Imran |
| 2008/0147143 A1 | 6/2008 | Popovic et al. |
| 2008/0154329 A1 | 6/2008 | Pyles et al. |
| 2008/0183224 A1 | 7/2008 | Barolat |
| 2008/0200749 A1 | 8/2008 | Zheng et al. |
| 2008/0202940 A1 | 8/2008 | Jiang et al. |
| 2008/0207985 A1 | 8/2008 | Farone |
| 2008/0208287 A1 | 8/2008 | Palermo et al. |
| 2008/0215113 A1 | 9/2008 | Pawlowicz |
| 2008/0221653 A1 | 9/2008 | Agrawal et al. |
| 2008/0224226 A1 | 9/2008 | Suzuki et al. |
| 2008/0228241 A1 | 9/2008 | Sachs |
| 2008/0228250 A1 | 9/2008 | Mironer |
| 2008/0234121 A1 | 9/2008 | Kim et al. |
| 2008/0234791 A1 | 9/2008 | Arle et al. |
| 2008/0279896 A1 | 11/2008 | Heinen et al. |
| 2008/0294211 A1 | 11/2008 | Moffitt |
| 2008/0294226 A1 | 11/2008 | Moffitt et al. |
| 2009/0012436 A1 | 1/2009 | Lanfermann et al. |
| 2009/0024997 A1 | 1/2009 | Kobayashi |
| 2009/0093854 A1 | 4/2009 | Leung et al. |
| 2009/0112281 A1 | 4/2009 | Miyazawa et al. |
| 2009/0118365 A1 | 5/2009 | Benson, III et al. |
| 2009/0131995 A1 | 5/2009 | Sloan et al. |
| 2009/0157141 A1 | 6/2009 | Chiao et al. |
| 2009/0198305 A1 | 8/2009 | Naroditsky et al. |
| 2009/0204173 A1 | 8/2009 | Fang et al. |
| 2009/0229166 A1 | 9/2009 | Sawrie |
| 2009/0270960 A1 | 10/2009 | Zhao et al. |
| 2009/0281529 A1 | 11/2009 | Carriazo |
| 2009/0281599 A1 | 11/2009 | Thacker et al. |
| 2009/0293270 A1 | 12/2009 | Brindley et al. |
| 2009/0299166 A1 | 12/2009 | Nishida et al. |
| 2009/0299167 A1 | 12/2009 | Seymour |
| 2009/0306491 A1 | 12/2009 | Haggers |
| 2010/0004715 A1 | 1/2010 | Fahey |
| 2010/0010646 A1 | 1/2010 | Drew et al. |
| 2010/0023103 A1 | 1/2010 | Elborno |
| 2010/0029040 A1 | 2/2010 | Nomoto |
| 2010/0042193 A1 | 2/2010 | Slavin |
| 2010/0070007 A1 | 3/2010 | Parker et al. |
| 2010/0114205 A1 | 5/2010 | Donofrio et al. |
| 2010/0114239 A1 | 5/2010 | McDonald, III |
| 2010/0125313 A1 | 5/2010 | Lee et al. |
| 2010/0137238 A1 | 6/2010 | Gan et al. |
| 2010/0137938 A1 | 6/2010 | Kishawi et al. |
| 2010/0145428 A1 | 6/2010 | Cameron et al. |
| 2010/0152811 A1 | 6/2010 | Flaherty |
| 2010/0166546 A1 | 7/2010 | Mahan et al. |
| 2010/0168820 A1 | 7/2010 | Maniak et al. |
| 2010/0185253 A1 | 7/2010 | Dimarco et al. |
| 2010/0198298 A1 | 8/2010 | Glukhovsky et al. |
| 2010/0217355 A1 | 8/2010 | Tass et al. |
| 2010/0228310 A1 | 9/2010 | Shuros et al. |
| 2010/0241121 A1 | 9/2010 | Logan et al. |
| 2010/0241191 A1 | 9/2010 | Testerman et al. |
| 2010/0268299 A1 | 10/2010 | Farone |
| 2010/0274312 A1 | 10/2010 | Alataris et al. |
| 2010/0280570 A1 | 11/2010 | Sturm et al. |
| 2010/0305660 A1 | 12/2010 | Hegi et al. |
| 2010/0312304 A1 | 12/2010 | York et al. |
| 2010/0318168 A1 | 12/2010 | Bighetti |
| 2010/0331925 A1 | 12/2010 | Peterson |
| 2011/0006793 A1 | 1/2011 | Peschke et al. |
| 2011/0009919 A1 | 1/2011 | Carbunaru et al. |
| 2011/0016081 A1 | 1/2011 | Basak et al. |
| 2011/0029040 A1 | 2/2011 | Walker et al. |
| 2011/0029044 A1 | 2/2011 | Hyde et al. |
| 2011/0034277 A1 | 2/2011 | Brandes |
| 2011/0034977 A1 | 2/2011 | Janik et al. |
| 2011/0040349 A1 | 2/2011 | Graupe |
| 2011/0054567 A1 | 3/2011 | Lane et al. |
| 2011/0054568 A1 | 3/2011 | Lane et al. |
| 2011/0054570 A1 | 3/2011 | Lane |
| 2011/0054579 A1 | 3/2011 | Kumar et al. |
| 2011/0077660 A1 | 3/2011 | Janik et al. |
| 2011/0082515 A1 | 4/2011 | Libbus et al. |
| 2011/0084489 A1 | 4/2011 | Kaplan |
| 2011/0093043 A1 | 4/2011 | Torgerson et al. |
| 2011/0112601 A1 | 5/2011 | Meadows et al. |
| 2011/0125203 A1 | 5/2011 | Simon et al. |
| 2011/0130804 A1 | 6/2011 | Lin et al. |
| 2011/0152967 A1 | 6/2011 | Simon et al. |
| 2011/0160810 A1 | 6/2011 | Griffith |
| 2011/0166546 A1 | 7/2011 | Jaax et al. |
| 2011/0184482 A1 | 7/2011 | Eberman et al. |
| 2011/0184488 A1 | 7/2011 | De Ridder |
| 2011/0184489 A1 | 7/2011 | Nicolelis et al. |
| 2011/0202107 A1 | 8/2011 | Sunagawa et al. |
| 2011/0208265 A1 | 8/2011 | Erickson et al. |
| 2011/0213266 A1 | 9/2011 | Williams et al. |
| 2011/0218590 A1 | 9/2011 | Degiorgio et al. |
| 2011/0218594 A1 | 9/2011 | Doron et al. |
| 2011/0224153 A1 | 9/2011 | Levitt et al. |
| 2011/0224665 A1 | 9/2011 | Crosby et al. |
| 2011/0224752 A1 | 9/2011 | Rolston et al. |
| 2011/0224753 A1 | 9/2011 | Palermo et al. |
| 2011/0224757 A1 | 9/2011 | Zdeblick et al. |
| 2011/0230101 A1 | 9/2011 | Tang et al. |
| 2011/0230701 A1 | 9/2011 | Simon et al. |
| 2011/0230702 A1 | 9/2011 | Honour |
| 2011/0231326 A1 | 9/2011 | Marino |
| 2011/0237221 A1 | 9/2011 | Prakash et al. |
| 2011/0237921 A1 | 9/2011 | Prakash et al. |
| 2011/0245734 A1 | 10/2011 | Wagner et al. |
| 2011/0276107 A1 | 11/2011 | Simon et al. |
| 2011/0288609 A1 | 11/2011 | Tehrani et al. |
| 2011/0295100 A1 | 12/2011 | Hegde et al. |
| 2012/0006793 A1 | 1/2012 | Swanson |
| 2012/0011950 A1 | 1/2012 | Kracke |
| 2012/0013041 A1 | 1/2012 | Cao et al. |
| 2012/0013126 A1 | 1/2012 | Molloy |
| 2012/0029528 A1 | 2/2012 | MacDonald et al. |
| 2012/0035684 A1 | 2/2012 | Thompson et al. |
| 2012/0041518 A1 | 2/2012 | Kim et al. |
| 2012/0052432 A1 | 3/2012 | Matsuura |
| 2012/0059432 A1 | 3/2012 | Emborg et al. |

(56) References Cited

U.S. PATENT DOCUMENTS

| | | |
|---|---|---|
| 2012/0071250 A1 | 3/2012 | O'Neil et al. |
| 2012/0071950 A1 | 3/2012 | Archer |
| 2012/0101326 A1 | 4/2012 | Simon et al. |
| 2012/0109251 A1 | 5/2012 | Lebedev et al. |
| 2012/0109295 A1 | 5/2012 | Fan |
| 2012/0116476 A1 | 5/2012 | Kothandaraman |
| 2012/0123223 A1 | 5/2012 | Freeman et al. |
| 2012/0123293 A1 | 5/2012 | Shah et al. |
| 2012/0126392 A1 | 5/2012 | Kälvesten et al. |
| 2012/0136408 A1 | 5/2012 | Grill et al. |
| 2012/0165899 A1 | 6/2012 | Gliner |
| 2012/0172222 A1 | 7/2012 | Artigas Puerto |
| 2012/0172246 A1 | 7/2012 | Nguyen et al. |
| 2012/0172946 A1 | 7/2012 | Alataris et al. |
| 2012/0179222 A1 | 7/2012 | Jaax et al. |
| 2012/0185020 A1 | 7/2012 | Simon et al. |
| 2012/0197338 A1 | 8/2012 | Su et al. |
| 2012/0203055 A1 | 8/2012 | Pletnev |
| 2012/0203131 A1 | 8/2012 | DiLorenzo |
| 2012/0221073 A1 | 8/2012 | Southwell et al. |
| 2012/0232615 A1 | 9/2012 | Barolat et al. |
| 2012/0252874 A1 | 10/2012 | Feinstein et al. |
| 2012/0259380 A1 | 10/2012 | Pyles |
| 2012/0271372 A1 | 10/2012 | Osorio |
| 2012/0277824 A1 | 11/2012 | Li |
| 2012/0277834 A1 | 11/2012 | Mercanzini et al. |
| 2012/0283697 A1 | 11/2012 | Kim et al. |
| 2012/0302821 A1 | 11/2012 | Burnett |
| 2012/0310305 A1 | 12/2012 | Kaula et al. |
| 2012/0310315 A1 | 12/2012 | Savage et al. |
| 2012/0330321 A1 | 12/2012 | Johnson et al. |
| 2013/0012853 A1 | 1/2013 | Brown |
| 2013/0013041 A1 | 1/2013 | Glukhovsky et al. |
| 2013/0026640 A1 | 1/2013 | Ito et al. |
| 2013/0030312 A1 | 1/2013 | Keel et al. |
| 2013/0030319 A1 | 1/2013 | Hettrick et al. |
| 2013/0030501 A1 | 1/2013 | Feler et al. |
| 2013/0035745 A1 | 2/2013 | Ahmed et al. |
| 2013/0053734 A1 | 2/2013 | Barriskill et al. |
| 2013/0053922 A1 | 2/2013 | Ahmed et al. |
| 2013/0066392 A1 | 3/2013 | Simon et al. |
| 2013/0085317 A1 | 4/2013 | Feinstein |
| 2013/0085361 A1 | 4/2013 | Mercanzini et al. |
| 2013/0096640 A1 | 4/2013 | Possover |
| 2013/0096661 A1 | 4/2013 | Greenberg et al. |
| 2013/0096662 A1 | 4/2013 | Swanson |
| 2013/0110196 A1 | 5/2013 | Alataris et al. |
| 2013/0116751 A1 | 5/2013 | Moffitt et al. |
| 2013/0123568 A1 | 5/2013 | Hamilton et al. |
| 2013/0123659 A1 | 5/2013 | Bartol et al. |
| 2013/0138167 A1 | 5/2013 | Bradley et al. |
| 2013/0165991 A1 | 6/2013 | Kim et al. |
| 2013/0197408 A1 | 8/2013 | Goldfarb et al. |
| 2013/0204324 A1 | 8/2013 | Thacker et al. |
| 2013/0211477 A1 | 8/2013 | Cullen et al. |
| 2013/0253222 A1 | 9/2013 | Nakao |
| 2013/0253229 A1 | 9/2013 | Sawant et al. |
| 2013/0253299 A1 | 9/2013 | Weber et al. |
| 2013/0253611 A1 | 9/2013 | Lee et al. |
| 2013/0268016 A1 | 10/2013 | Xi et al. |
| 2013/0268021 A1 | 10/2013 | Moffitt |
| 2013/0281890 A1 | 10/2013 | Mishelevich |
| 2013/0289446 A1 | 10/2013 | Stone et al. |
| 2013/0289667 A1 | 10/2013 | Wacnik et al. |
| 2013/0303873 A1 | 11/2013 | Vörös et al. |
| 2013/0304159 A1 | 11/2013 | Simon et al. |
| 2013/0310211 A1 | 11/2013 | Wilton et al. |
| 2013/0310911 A1 | 11/2013 | Tai et al. |
| 2014/0005753 A1 | 1/2014 | Carbunaru |
| 2014/0031893 A1 | 1/2014 | Walker et al. |
| 2014/0046407 A1 | 2/2014 | Ben-Ezra et al. |
| 2014/0058292 A1 | 2/2014 | Alford et al. |
| 2014/0058490 A1 | 2/2014 | DiMarco |
| 2014/0066950 A1 | 3/2014 | MacDonald et al. |
| 2014/0067007 A1 | 3/2014 | Drees et al. |
| 2014/0067354 A1 | 3/2014 | Kaula et al. |
| 2014/0074190 A1 | 3/2014 | Griffith |
| 2014/0081011 A1 | 3/2014 | Vaught |
| 2014/0081071 A1 | 3/2014 | Simon et al. |
| 2014/0088674 A1 | 3/2014 | Bradley |
| 2014/0100633 A1 | 4/2014 | Mann et al. |
| 2014/0107397 A1 | 4/2014 | Simon et al. |
| 2014/0107398 A1 | 4/2014 | Simon et al. |
| 2014/0114374 A1 | 4/2014 | Rooney et al. |
| 2014/0163640 A1 | 6/2014 | Edgerton et al. |
| 2014/0172045 A1 | 6/2014 | Yip et al. |
| 2014/0180361 A1 | 6/2014 | Burdick et al. |
| 2014/0213842 A1 | 7/2014 | Simon et al. |
| 2014/0228905 A1 | 8/2014 | Bolea |
| 2014/0236257 A1 | 8/2014 | Parker et al. |
| 2014/0243923 A1 | 8/2014 | Doan et al. |
| 2014/0277271 A1 | 9/2014 | Chan et al. |
| 2014/0296752 A1 | 10/2014 | Edgerton et al. |
| 2014/0303901 A1 | 10/2014 | Sadeh |
| 2014/0316484 A1 | 10/2014 | Edgerton et al. |
| 2014/0316503 A1 | 10/2014 | Tai et al. |
| 2014/0324118 A1 | 10/2014 | Simon et al. |
| 2014/0330067 A1 | 11/2014 | Jordan |
| 2014/0330335 A1 | 11/2014 | Errico et al. |
| 2014/0336722 A1 | 11/2014 | Rocon De Lima et al. |
| 2014/0357936 A1 | 12/2014 | Simon et al. |
| 2015/0005840 A1 | 1/2015 | Pal et al. |
| 2015/0065559 A1 | 3/2015 | Feinstein et al. |
| 2015/0066111 A1 | 3/2015 | Blum et al. |
| 2015/0165226 A1 | 6/2015 | Simon et al. |
| 2015/0182784 A1 | 7/2015 | Barriskill et al. |
| 2015/0190634 A1 | 7/2015 | Rezai et al. |
| 2015/0196231 A1 | 7/2015 | Ziale et al. |
| 2015/0217120 A1 | 8/2015 | Nandra et al. |
| 2015/0231396 A1 | 8/2015 | Burdick et al. |
| 2015/0265830 A1 | 9/2015 | Simon et al. |
| 2015/0328462 A1 | 11/2015 | Griffith |
| 2016/0001096 A1 | 1/2016 | Mishelevich |
| 2016/0030737 A1 | 2/2016 | Gerasimenko et al. |
| 2016/0030748 A1 | 2/2016 | Edgerton et al. |
| 2016/0030750 A1 | 2/2016 | Bokil et al. |
| 2016/0045727 A1 | 2/2016 | Rezai et al. |
| 2016/0045731 A1 | 2/2016 | Simon et al. |
| 2016/0074663 A1 | 3/2016 | De Ridder |
| 2016/0121114 A1 | 5/2016 | Simon et al. |
| 2016/0121116 A1 | 5/2016 | Simon et al. |
| 2016/0143588 A1 | 5/2016 | Hoitink et al. |
| 2016/0157389 A1 | 6/2016 | Hwang |
| 2016/0220813 A1 | 8/2016 | Edgerton et al. |
| 2016/0235977 A1 | 8/2016 | Lu et al. |
| 2016/0279418 A1 | 9/2016 | Courtine et al. |
| 2016/0279429 A1 | 9/2016 | Hershey et al. |
| 2016/0310739 A1 | 10/2016 | Burdick et al. |
| 2017/0128729 A1 | 5/2017 | Netoff et al. |
| 2017/0007831 A1 | 6/2017 | Edgerton et al. |
| 2017/0157389 A1 | 6/2017 | Tai et al. |
| 2017/0157396 A1 | 6/2017 | Dixon et al. |
| 2017/0161454 A1 | 6/2017 | Grill et al. |
| 2017/0165497 A1 | 6/2017 | Lu |
| 2017/0173326 A1* | 6/2017 | Bloch ............... A61N 1/36139 |
| 2017/0246450 A1 | 8/2017 | Liu et al. |
| 2017/0246452 A1 | 8/2017 | Liu et al. |
| 2017/0266455 A1 | 9/2017 | Steinke |
| 2017/0274209 A1 | 9/2017 | Edgerton et al. |
| 2017/0296837 A1 | 10/2017 | Jin |
| 2017/0354819 A1 | 12/2017 | Bloch et al. |
| 2017/0361093 A1 | 12/2017 | Yoo et al. |
| 2018/0056078 A1 | 3/2018 | Kashyap et al. |
| 2018/0085583 A1 | 3/2018 | Zhang et al. |
| 2018/0104479 A1 | 4/2018 | Grill et al. |
| 2018/0110992 A1 | 4/2018 | Parramon et al. |
| 2018/0125416 A1 | 5/2018 | Schwarz et al. |
| 2018/0178008 A1 | 6/2018 | Bouton et al. |
| 2018/0185642 A1 | 7/2018 | Lu |
| 2018/0185648 A1 | 7/2018 | Nandra et al. |
| 2018/0193655 A1 | 7/2018 | Zhang et al. |
| 2018/0229037 A1 | 8/2018 | Edgerton et al. |
| 2018/0229038 A1 | 8/2018 | Burdick et al. |
| 2018/0236240 A1 | 8/2018 | Harkema et al. |

(56) References Cited

U.S. PATENT DOCUMENTS

| | | |
|---|---|---|
| 2018/0256906 A1 | 9/2018 | Pivonka et al. |
| 2018/0280693 A1 | 10/2018 | Edgerton et al. |
| 2018/0353755 A1 | 12/2018 | Edgerton et al. |
| 2018/0361146 A1 | 12/2018 | Gerasimenko et al. |
| 2019/0022371 A1 | 1/2019 | Chang et al. |
| 2019/0033622 A1 | 1/2019 | Olgun et al. |
| 2019/0160294 A1 | 5/2019 | Peterson et al. |
| 2019/0167987 A1 | 6/2019 | Lu et al. |
| 2019/0192864 A1 | 6/2019 | Koop et al. |
| 2019/0247650 A1 | 8/2019 | Tran |
| 2019/0269917 A1 | 9/2019 | Courtine et al. |
| 2019/0381313 A1 | 12/2019 | Lu |
| 2019/0381328 A1 | 12/2019 | Wechter et al. |
| 2020/0155865 A1 | 5/2020 | Lu |
| 2020/0228901 A1 | 7/2020 | Baek |
| 2021/0069052 A1 | 3/2021 | Burke |
| 2021/0187278 A1 | 6/2021 | Lu |
| 2021/0236837 A1 | 8/2021 | Lu |
| 2021/0378991 A1 | 12/2021 | Lu et al. |

FOREIGN PATENT DOCUMENTS

| | | |
|---|---|---|
| CA | 2864473 A1 | 5/2013 |
| CA | 2823592 A1 | 11/2021 |
| CN | 101227940 A | 7/2008 |
| CN | 103263727 A | 8/2013 |
| CN | 104307098 A | 1/2015 |
| EP | 0630987 A1 | 12/1994 |
| EP | 2130326 A1 | 12/2009 |
| EP | 2141851 A2 | 1/2010 |
| EP | 2160127 A1 | 3/2010 |
| EP | 2178319 A1 | 4/2010 |
| EP | 2192897 A1 | 6/2010 |
| EP | 2226114 A1 | 9/2010 |
| EP | 2258496 A1 | 12/2010 |
| EP | 2361631 A1 | 8/2011 |
| EP | 2368401 A1 | 9/2011 |
| EP | 2387467 A1 | 11/2011 |
| EP | 2396995 A1 | 12/2011 |
| EP | 2397788 A1 | 12/2011 |
| EP | 2445990 A2 | 5/2012 |
| EP | 2471518 A2 | 7/2012 |
| EP | 2475283 A1 | 7/2012 |
| EP | 2486897 A2 | 8/2012 |
| EP | 2626051 A1 | 8/2013 |
| EP | 2628502 A1 | 8/2013 |
| EP | 2661307 A2 | 11/2013 |
| EP | 2688642 A2 | 1/2014 |
| EP | 2810689 A1 | 12/2014 |
| EP | 2810690 A1 | 12/2014 |
| EP | 2868343 A1 | 5/2015 |
| EP | 2966422 A1 | 1/2016 |
| EP | 2968940 A1 | 1/2016 |
| EP | 3184145 A1 | 6/2017 |
| EP | 3323468 A1 | 5/2018 |
| EP | 3328481 A1 | 6/2018 |
| EP | 3527258 A1 | 8/2019 |
| JP | H0326620 A | 2/1991 |
| JP | 3184145 B2 | 7/2001 |
| JP | 2002200178 A | 7/2002 |
| JP | 2007526798 A | 9/2007 |
| JP | 2008067917 A | 3/2008 |
| JP | 2008543429 A | 12/2008 |
| JP | 2014514043 A | 6/2014 |
| JP | 6132856 B2 | 3/2015 |
| JP | 2016506255 A | 3/2016 |
| JP | 2017104685 A | 6/2017 |
| JP | 2017525509 A | 9/2017 |
| JP | 2018524113 A | 8/2018 |
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2193441 C2 | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2475283 C2 | 2/2013 |
| RU | 2661307 C1 | 7/2018 |
| WO | 97047357 A1 | 12/1997 |
| WO | 02034331 A1 | 5/2002 |
| WO | 02092165 A1 | 11/2002 |
| WO | 03005887 A2 | 1/2003 |
| WO | 03026735 A2 | 4/2003 |
| WO | 03092795 A1 | 11/2003 |
| WO | 2004087116 A2 | 10/2004 |
| WO | 2005002663 A2 | 1/2005 |
| WO | 2005051306 A2 | 6/2005 |
| WO | 2005065768 A1 | 7/2005 |
| WO | 2005087307 A2 | 9/2005 |
| WO | 2006138069 A1 | 12/2006 |
| WO | 2007007058 A1 | 1/2007 |
| WO | 2007012114 A1 | 2/2007 |
| WO | 2007047852 A2 | 4/2007 |
| WO | 2007081764 A2 | 7/2007 |
| WO | 2007107831 A2 | 9/2007 |
| WO | 2008070807 A3 | 6/2008 |
| WO | 2008075294 A1 | 6/2008 |
| WO | 2008109862 A2 | 9/2008 |
| WO | 2008121891 A1 | 10/2008 |
| WO | 2009042217 A1 | 4/2009 |
| WO | 2009111142 A2 | 9/2009 |
| WO | 2010021977 A1 | 2/2010 |
| WO | 2010055421 A1 | 5/2010 |
| WO | 2010114998 A1 | 10/2010 |
| WO | 2010124128 A1 | 10/2010 |
| WO | 2011005607 A1 | 1/2011 |
| WO | 2011136875 A1 | 11/2011 |
| WO | 2012050200 A1 | 4/2012 |
| WO | 2012075195 A1 | 6/2012 |
| WO | 2012080964 A1 | 6/2012 |
| WO | 2012094346 A2 | 7/2012 |
| WO | 2012100260 A2 | 7/2012 |
| WO | 2012129574 A2 | 9/2012 |
| WO | 2013071307 A1 | 5/2013 |
| WO | 2013071309 A1 | 5/2013 |
| WO | 2013152124 A1 | 10/2013 |
| WO | 2013179230 A1 | 12/2013 |
| WO | 2013188965 A1 | 12/2013 |
| WO | 2014005075 A1 | 1/2014 |
| WO | 2014031142 A1 | 2/2014 |
| WO | 2014089299 A2 | 6/2014 |
| WO | 2014144785 A1 | 9/2014 |
| WO | 2014149895 A1 | 9/2014 |
| WO | 2014205356 A2 | 12/2014 |
| WO | 2014209877 A1 | 12/2014 |
| WO | 2015000800 A1 | 1/2015 |
| WO | 2015048563 A2 | 4/2015 |
| WO | 2015063127 A1 | 5/2015 |
| WO | 2015106286 A1 | 7/2015 |
| WO | 2016029159 A2 | 2/2016 |
| WO | 2016033369 A1 | 3/2016 |
| WO | 2016033372 A1 | 3/2016 |
| WO | 2016064761 A1 | 4/2016 |
| WO | 2016110804 A1 | 7/2016 |
| WO | 2016112398 A1 | 7/2016 |
| WO | 2016172239 A1 | 10/2016 |
| WO | 2017011410 A1 | 1/2017 |
| WO | 2017024276 A1 | 2/2017 |
| WO | 2017035512 A1 | 3/2017 |
| WO | 2017044904 A1 | 3/2017 |
| WO | 2017058913 A1 | 4/2017 |
| WO | 2017062508 A1 | 4/2017 |
| WO | 2017117450 A1 | 7/2017 |
| WO | 2017146659 A1 | 8/2017 |
| WO | 2018039296 A2 | 3/2018 |
| WO | 2018106843 A1 | 6/2018 |

(56) References Cited

FOREIGN PATENT DOCUMENTS

| WO | 2018160531 A1 | 8/2018 |
| --- | --- | --- |
| WO | 2018217791 A1 | 11/2018 |
| WO | 2019211314 A1 | 11/2019 |
| WO | 2020041502 A1 | 2/2020 |
| WO | 2020041633 A1 | 2/2020 |
| WO | 2020236946 A1 | 11/2020 |

OTHER PUBLICATIONS

Rattay, F. et al., "Epidural electrical stimulation of posterior structures of the human lumbosacral cord: 2. quantitative analysis by computer modeling," Spinal Cord, vol. 38, No. 8, Aug. 2000, 17 pages.

Minassian, K. et al., "Stepping-like movements in humans with complete spinal cord injury induced by epidural stimulation of the lumbar cord: electromyographic study of compound muscle action potentials," Spinal Cord, vol. 42, No. 7, Jul. 2004, Published Online May 4, 2004, 16 pages.

Gerasimenko, Y. et al., "Spinal cord reflexes induced by epidural spinal cord stimulation in normal awake rats," Journal of Neuroscience Methods, vol. 157, No. 2, Oct. 30, 2006, Published Online Jun. 9, 2006, 11 pages.

Harkema, S. et al., "Effect of Epidural stimulation of the lumbosacral spinal cord on voluntary movement, standing, and assisted stepping after motor complete paraplegia: a case study," Lancet, vol. 377, No. 9781, Jun. 4, 2011, Available Online May 19, 2011, 17 pages.

Van Den Brand, R. et al., "Restoring Voluntary Control of Locomotion after Paralyzing Spinal Cord Injury," Science Magazine, vol. 336, No. 6085, Jun. 1, 2012, 5 pages.

Capogrosso, M. et al., "A Computational Model for Epidural Electrical Stimulation of Spinal Sensorimotor Circuits," Journal of Neuroscience, vol. 33, No. 49, Dec. 4, 2013, 15 pages.

Levine, A. et al., "Identification of cellular node for motor control pathways," Nature Neuroscience, vol. 17, No. 4, Apr. 2014, Available Online Mar. 9, 2014, 22 pages.

Angeli, C. et al., "Altering spinal cord excitability enables voluntary movements after chronic complete paralysis in humans," Brain: A Journal of Neurology, vol. 137, No. 5, May 1, 2014, Published Online Apr. 8, 2014, 16 pages.

Danner, S. et al., "Human spinal locomotor control is based on flexibly organized burst generators," Brain: A Journal of Neurology, vol. 138, No. 3, Mar. 1, 2015, Published Online Jan. 12, 2015, 12 pages.

Shamir, R. et al., "Machine learning approach to optimizing combined stimulation and medication therapies for Parkinson's disease," Brain Stimulation, vol. 8, No. 6, Nov. 2015, Published Online Jun. 15, 2015, 22 pages.

Gerasimenko, Y. et al., "Noninvasive Reactivation of Motor Descending Control after Paralysis," Journal of Neurotrauma, vol. 32, No. 24, Dec. 15, 2015, Published Online Aug. 20, 2015, 13 pages.

Wenger, N. et al., "Spatiotemporal neuromodulation therapies engaging muscle synergies improve motor control after spinal cord injury," Natural Medicine, vol. 22, No. 2, Feb. 2016, Available Online Jan. 18, 2016, 33 pages.

Moraud, E. et al., "Mechanisms Underlying the Neuromodulation of Spinal Circuits for Correcting Gait and Balance Deficits after Spinal Cord Injury," Neuron, vol. 89, No. 4, Feb. 17, 2016, Available Online Feb. 4, 2016, 16 pages.

Capogrosso, M. et al., "A Brain-Spinal Interface Alleviating Gait Deficits after Spinal Cord Injury in Primates," Nature, vol. 539, No. 7628, Nov. 10, 2016, 39 pages.

ISA European Patent Office, International Search Report and Written Opinion Issued in Application No. PCT/EP2018/082942, Feb. 14, 2019, WIPO, 12 pages.

European Patent Office, Office Action Issued in Application No. 18807366.2, Mar. 22, 2023, Germany, 4 pages.

Fleshman, J. et al., "Electronic Architecture of Type-Identified a-Motoneurons in the Cat Spinal Cord," Journal of Neurophysiology, vol. 60, No. 1, Jul. 1, 1988, 26 pages.

Harrison, P. et al., "Individual Excitatory Post-Synaptic Potentials Due to Muscle Spindle la Afferents in Cat Triceps Surae Motoneurones," The Journal of Physiology, vol. 312, No. 1, (Mar. 1981), 16 pages.

Hines, M. et al., "The Neuron Simulation Environment," Neural Computation, vol. 9, No. 6, Aug. 15, 1997, 26 pages.

Jones, K. et al., "Computer Simulation of the Responses of Human Motoneurons to Composite 1A EPSPS: Effects of Background Firing Rate," The Journal of Physiology, vol. 77, No. 1, 1997, 16 pages.

Prochazka, A. et al., "Ensemble firing of muscle afferents recorded during normal locomotion in cats," The Journal of Physiology, vol. 507, No. 1, Feb. 15, 1998, 12 pages.

Prochazka, A. et al., "Models of ensemble filing of muscle spindle afferents recorded during normal locomotion in cats," The Journal of Physiology, vol. 507, No. 1, Feb. 15, 1998, 15 pages.

Mcintyre, C. et al., "Modeling the Excitability of Mammalian Nerve Fibers: Influence of Afterpotentials on the Recovery Cycle," Journal of Neurophysiology, vol. 87, No. 2, Feb. 2002, 12 pages.

Anderson, K., "Targeting Recovery: Priorities of the Spinal Cord-Injured Population," Journal of Neurotrauma, vol. 21, No. 10, Oct. 2004, 13 pages.

Minassian, K. et al., "Human lumbar cord circuitries can be activated by extrinsic tonic input to generate locomotor-like activity," Human Movement Science, vol. 26, No. 2, 2007, 21 pages.

Rodger, D. et al., "High Density Flexible Parylene-Based Multielectrode Arrays for Retinal and Spinal Cord Stimulation," Proceedings of the 14th International Conference on Solid-State Sensors, Actuators and Microsystems, 2007, 4 pages.

Stienen, A. et al., "Analysis of reflex modulation with a biologically realistic neural network," Journal of Computer Neuroscience, vol. 23, No. 3, Dec. 2007, Available Online May 15, 2007, 16 pages.

Krassioukov, A. et al., "A Systematic Review of the Management of Autonomic Dysreflexia Following Spinal Cord Injury," Archives of Physical Medicine and Rehabilitation, vol. 90, No. 4, Apr. 2009, 27 pages.

Krassioukov, A. et al., "A Systematic Review of the Management of Orthostatic Hypotension Following Spinal Cord Injury," Archives of Physical Medicine and Rehabilitation, vol. 90, No. 5, May 2009, 22 pages.

Johnson, W. et al., "Application of a Rat Hindlimb Model: A Prediction of Force Spaces Reachable Through Stimulation of Nerve Fascicles," IEEE Transactions on Bio-Medical Engineering, vol. 58, No. 12, Dec. 2011, Available Online Jan. 17, 2011, 22 pages.

Hennig, P. et al., "Entropy search for information-efficient global optimization," Journal of Machine Learning Research (JMLR), vol. 13, Jun. 2012, 29 pages.

Gilja, V. et al., "A high-performance neural prosthesis enabled by control algorithm design," Nature Neuroscience, vol. 15, No. 12, Dec. 2012, Published Online Nov. 18, 2012, 56 pages.

Minassian, K. et al., "Neuromodulation of lower limb motor control in restorative neurology," Clinical Neurology and Neurosurgery, vol. 114, 2012, 9 pages.

Ryzhov, I. O. et al., "The knowledge gradient algorithm for a general class of online learning problems," Operations Research, vol. 60, No. 1, 2012, 47 pages.

Lozano, A. et al., "Probing and Regulating Dysfunctional Circuits Using Deep Brain Stimulation," Neuron, vol. 77, No. 3, Feb. 6, 2013, 19 pages.

Minassian et al., "Mechanisms of rhythm generation of the human lumbar spinal cord in repose to tonic stimulation without and with step-related sensory feedback," Biomedizinische Technik, vol. 58, (Suppl. 1), 2013, 3 pages.

Hofstoetter, U. et al., "Effects of transcutaneous spinal cord stimulation on voluntary locomotor activity in an incomplete spinal cord injured individual," Biomedizinische Technik, vol. 58, Suppl. 1, 2013, 3 pages.

(56) References Cited

OTHER PUBLICATIONS

Sayenko, D. et al., "Neuromodulation of evoked muscle potentials induced by epidural spinal-cord stimulation in paralyzed individuals," Journal of Neurophysiology, vol. 111, No. 5, 2014, Published Online Dec. 11, 2013, 12 pages.
Nandra, M. et al., "Microelectrode Implants for Spindal Cord Stimulation in Rats," Doctor of Philosophy Thesis, California Institute of Technology, 2014, 104 pages.
Wan, D. et al., "Life-threatening outcomes associated with autonomic dysreflexia: A clinical review," Journal of Spinal Cord Medicine, vol. 37, No. 1, Jan. 2014, 9 pages.
Phillips, A. et al., "Perturbed and spontaneous regional cerebral blood flow responses to changes in blood pressure secondary high-level spinal cord injury: the effect of midodrine," Journal of Applied Physiology, vol. 116, No. 6, Mar. 15, 2014. Available Online Jan. 16, 2014, 9 pages.
Phillips, A. et al., "Regional neurovascular coupling and cognitive performance in those with low blood pressure secondary to high-level spinal cord injury: improved by alpha-1 agonist midodrine hydrochloride," Journal of Cerebral Blood Flow & Metabolism, vol. 34, No. 5, May 2014, 8 pages.
Zhang, T. et al., "Mechanisms and models of spinal cord stimulation for the treatment of neuropathic pain," Brain Research, vol. 1569, Jun. 20, 2014, Published Online May 4, 2014, 14 pages.
Wenger, N. et al. "Closed-loop neuromodulation of spinal sensorimotor circuits controls refined locomotion after complete spinal cord injury," Science Translational Medicine, Sep. 24, 2014, vol. 6, No. 255, 10 pages.
Wenger, N. et al., "Supplementary Materials for Closed-loop neuromodulation of spinal sensorimotor circuits controls refined locomotion after complete spinal cord injury," Science Translational Medicine, vol. 6, No. 255, Sep. 24, 2014, 14 pages.
Hofstoetter, U. et al., "Modification of spasticity by transcutaneous spinal cord stimulation in individuals with incomplete spinal cord injury," The Journal of Spinal Cord Medicine, vol. 37, No. 2, 2014, 10 pages.
Takeoka, A. et al., "Muscle Spindle Feedback Directs Locomotor Recovery and Circuit Reorganization after Spinal Cord Injury," Cell, vol. 159, No. 7, Dec. 18, 2014, 27 pages.
Minev, I. et al., "Electronic dura mater for long-term multimodal neural interfaces," Science Magazine, vol. 347, No. 6218, Jan. 9, 2015, 64 pages.
Phillips, A. et al., "Contemporary Cardiovascular Concerns after Spinal Cord Injury: Mechanisms, Maladaptations, and Management," Journal of Neurotrama, vol. 32, No. 24, Dec. 15, 2015, 17 pages.
Rejc, E. et al., "Effects of Lumbosacral Spinal Cord Epidural Stimulation for Standing after Chronic Complete Paralysis in Humans," PLoS One, vol. 10, No. 7, Jul. 24, 2015, 20 pages.
Jarosiewicz, B. et al., "Virtual typing by people with tetraplegia using a self-calibrating intracortical brain-computer interface," Science Translational Medicine, vol. 7, No. 313, Nov. 11, 2015, 11 pages.
Jarosiewicz, B. et al., "Supplementary Materials for Virtual typing by people with tetraplegia using a self-calibrating intracortical brain-computer interface," Science Translational Medicine, vol. 7, No. 313, Nov. 11, 2015, 26 pages.
Danner, S. M. et al., "Body Position Influences Which neural structures are recruited by lumbar transcutaneous spinal cord stimulation," PLoS ONE, vol. 11, No. 1, 2016, 13 pages.
Burke, R., "Group Ia Synaptic Input to Fast and Slow Twitch Motor Units of Cat Triceps Surae," The Journal of Physiology, vol. 196, No. 3, Jun. 1, 1968, 26 pages.
Cai, L. et al., "Implications of Assist-As-Needed Robotic Step Training after a Complete Spinal Cord Injury on Intrinsic Strategies of Motor Learning," The Journal of Neuroscience, vol. 26, No. 41, Oct. 11, 2006, 5 pages.
Courtine, G. et al., "Can experiments in nonhuman primates expedite the translation of treatments for spinal cord injury in humans?," Nature Medicine, vol. 13, No. 5, May 2007, 13 pages.

Drew, T. et al., "Cortical mechanisms involved in visuomotor coordination during precision walking," Brain Research Reviews, vol. 57, No. 1, Jan. 2007, Published Online Aug. 22, 2007, 13 pages.
Edgerton, V. et al., "Training Locomotor Networks," Brain Research Reviews, vol. 57, Jan. 2008, Published Online Sep. 16, 2007, 25 pages.
Kwakkel, G. et al., "Effects of Robot-assisted therapy on upper limb recovery after stroke: A Systematic Review," Neurorehabilitation and Neural Repair, vol. 22, No. 2, Mar. 2008, Published Online Sep. 17, 2007, 17 pages.
Lizotte, D. et al., "Automatic gait optimization with Gaussian process regression," Proceedings of the 20th international joint conference on Artifical intelligence (IJCAI), Jan. 6, 2007, Hyderabad, India, 6 pages.
Courtine, G. et al., "Recovery of supraspinal control of stepping via indirect propriospinal relay connections after spinal cord injury," Nature Medicine, vol. 14, No. 1, Jan. 6, 2008, 6 pages.
Cowley, K. et al., "Propriospinal neurons are sufficient for bulbospinal transmission of the locomotor command signal in the neonatal rat spinal cord," The Journal of Physiology, vol. 586, No. 6, Mar. 15, 2008, Published Online Jan. 31, 2008, 13 pages.
Krause, A. et al. "Near-Optimal Sensor Placements in Gaussian Processes: Theory, Efficient Algorithms and Empirical Studies," Journal of Machine Learning Research (JMLR), vol. 9, Feb. 2008, 8 pages.
Lavrov, I. et al., "Epidural Stimulation Induced Modulation of Spinal Locomotor Networks in Adult Spinal Rats," Journal of Neuroscience, vol. 28, No. 23, Jun. 4, 2008, 8 pages.
Vallery, H. et al., "Compliant Actuation of Rehabilitation Robots," IEEE Robotics & Automation Magazine, vol. 15, No. 3, Sep. 12, 2008, 10 pages.
Abernethy, J. et al., "Competing in the Dark: An Efficient Algorithm for Bandit Linear Optimization," Conference on Learning Theory, 2008, 13 pages.
Bubeck, S. et al., "Online Optimization in X-Armed Bandits," Advances in Neural Information Processing Systems (NIPS), 2008, 8 pages.
Ward, A. R., "Electrical Stimulation Using Kilohertz-Frequency Alternating Current," Physical Therapy, vol. 89, 2009, Published online Dec. 18, 2008, 10 pages.
Dani, V. et al., "Stochastic Linear Optimization Under Bandit Feedback," Proceedings of the 21st Annual Conference on Learning Theory (COLT), 2008, Helsinki, Finland, 15 pages.
Edgerton, V. et al., "Robotic Training and Spinal Cord Plasticity," Brain Research Bulletin, vol. 78, No. 1, Jan. 15, 2009, Published Online Nov. 14, 2008, 19 pages.
Hofstoetter, U. et al., "Modification of Reflex Responses to Lumbar Posterior Root Stimulation by Motor Tasks in Healthy Subjects," Artificial Organs, vol. 32, No. 8, 2008, 5 pages.
Kleinberg, R. et al., "Multi-armed bandits in metric spaces," Proceedings of the STOC, Computer and Automation Research Institute of the Hungarian Academy of Sciences, Budapest, Hungary, 2008, 26 pages.
Brochu, E. et al., "A Tutorial on Bayesian Optimization of Expensive Cost Functions, with Application to Active User Modeling and Hierarchical Reinforcement Learning," TR-2009-23, UBC, 2009, 49 pages.
Bubeck, S. et al., "Pure Exploration in Finitely-Armed and Continuous-Armed Bandits problems," ALT, 2009, 35 pages.
Fuentes, R. et al., "Spinal Cord Stimulation Restores Locomotion in Animal Models of Parkinson's Disease," Science, vol. 323, No. 5921, Mar. 20, 2009, 14 pages.
Hofstoetter, U. et al., "Model of spinal cord reflex circuits in humans: Stimulation frequency-dependence of segmental activities and their interactions," Proceedings of the Second Congress International Society of Intraoperative Neurophysiology (ISIN), Dubrovnik, Croatia, 2009, 149 pages.
Courtine, G. et al., "Transformation of nonfunctional spinal circuits into functional states after the loss of brain input," Nature Neuroscience, vol. 12, No. 10, Oct. 2009, Published Online Sep. 20, 2009, 12 pages.

(56) References Cited

OTHER PUBLICATIONS

Minassian, K. et al., "Posterior root-muscle reflex," Proceedings of the Second Congress International Society of Intraoperative Neurophysiology (ISIN), Dubrovnik, Croatia, 2009, 6 pages.
Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Nov. 2009, Published Online Jul. 24, 2009, 5 pages.
Alto, L. et al., "Chemotropic Guidance Facilitates Axonal Regeneration and Synapse Formation after Spinal Cord Injury," Nature Neuroscience, vol. 12, No. 9, Sep. 2009, Published Online Aug. 2, 2009, 22 pages.
Azimi, J. et al., "Batch Bayesian Optimization via Simulation Matching," Proceedings of the Advances in Neural Information Processing Systems (NIPS), 2010, Vancouver, British Columbia, Canada, 9 pages.
Hagglund, M. et al., "Activation of groups of excitatory neurons in the mammalian spinal cord or hindbrain evokes locomotion," Nature Neuroscience, vol. 13, No. 2, Feb. 2010, Published Online Jan. 17, 2010, 8 pages.
Wessels, M. et al., "Body Weight-Supported Gait Training for Restoration of Walking in People with an Incomplete Spinal Cord Injury: A Systematic Review," Journal of Rehabilitation Medicine, vol. 42, No. 6, Jun. 2010, 7 pages.
Duschau-Wicke, A. et al., "Patient-cooperative control increases active participation of individuals with SCI during robot-aided gait training," Journal of NeuroEngineering and Rehabilitation, vol. 7, No. 43, Sep. 10, 2010, 13 pages.
Ladenbauer, J. et al., "Stimulation of the human lumbar spinal cord with implanted and surface electrodes: a computer simulation study," IEEE Transactions on Neural Systems and Rehabilitation Engineering, vol. 18, No. 6, 2010, 9 pages.
Minassian, K. et al., "Transcutaneous stimulation of the human lumbar spinal cord: Facilitating locomotor output in spinal cord injury," Proceedings of the Society for Neuroscience, Conference Proceedings, Neuroscience 2010, San Diego, CA, Abstract Viewer/Itinerary Planner No. 286. 19, Abstract & Poster Attached, 2010, 1 page.
Rasmussen, C. E. et al., "Gaussian Processes for Machine Learning (GPML) Toolbox," The Journal of Machine Learning Research, vol. 11, 2010, 9 pages.
Widmer, C. et al., "Inferring latent task structure for multitask learning by multiple kernel learning," BMC Bioinformatics, vol. 11, Suppl 8:S5, 2010, 8 pages.
Rosenzweig, E. et al., "Extensive Spontaneous Plasticity of Corticospinal Projections After Primate Spinal Cord Injury," Nature Neuroscience, vol. 13, No. 12, Dec. 2010, Published Online Nov. 14, 2010, 19 pages.
Srinivas, N. et al., "Gaussian process optimization in the bandit setting: No regret and experimental design," Proceedings of the 27th International Conference on Machine Learning, 2010, Haifa, Israel, 17 pages.
Tenne, Y. et al., "Computational Intelligence in Expensive Optimization Problems,"Adaptation, Learning, and Optimization, vol. 2, Springer, Berlin Heidelberg, 2010, 32 pages.
Zorner, B. et al., "Profiling locomotor recovery: comprehensive quantification of impairments after CNS damage in rodents," Nature Methods, vol. 7, No. 9, Sep. 2010, Published Online Aug. 15, 2010, 11 pages.
Ada, L. et al., "Mechanically assisted walking with body weight support results in more independent walking than assisted overground walking in non-ambulatory patients early after stroke: a systematic review," Journal of Physiotherapy, vol. 56, No. 3, Sep. 2010, 9 pages.
Hidler, J. et al., "ZeroG: Overground gait and balance training system," Journal of Rehabilitation Research & Development, vol. 48, No. 4, Available as Early as Jan. 1, 2011, 12 pages.
Krause, A. et al. "Contextual Gaussian Process Bandit Optimization", In Advances in Neural Information Processing Systems (NIPS), 2011, 9 pages.

Musselman, K. et al., "Spinal Cord Injury Functional Ambulation Profile: A New Measure of Walking Ability," Neurorehabilitation and Neural Repair, vol. 25, No. 3, Published Online Feb. 25, 2011, (Mar. 2011), 9 pages.
Wirz, M. et al., "Effectiveness of automated locomotor training in patients with acute incomplete spinal cord injury: A randomized controlled multicenter trial," BMC Neurology, vol. 11, No. 60, May 27, 2011, 9 pages.
Musienko, P. et al., "Controlling specific locomotor behaviors through multidimensional monoaminergic modulation of spinal circuitries," The Journal of Neuroscience, vol. 31, No. 25, Jun. 22, 2011, 32 pages.
Musienko, P. et al. "Multi-system neurorehabilitative strategies to restore motor functions following severe spinal cord injury," Experimental Neurology, vol. 235, No. 1, Published Online Sep. 7, 2011, (May 2012), 10 pages.
Nandra, M. S. et al., "A parylene-based microelectrode array implant for spinal cord stimulation in rats," Proceedings of the IEEE Engineering in Medicine and Biology Society, 2011, Boston, Massachusetts, 13 pages.
Sun, F. et al., "Sustained axon regeneration induced by co-deletion of PTEN and SOCS3," Nature, vol. 480, No. 7377, Dec. 15, 2011, Published Online Nov. 6, 2011, 12 pages.
Azimi, J. et al., "Hybrid Batch Bayesian Optimization," Proceedings of the 29th International Conference on Machine Learning, 2012, Edinburgh, Scotland, 12 pages.
Azimi, J. et al., "Batch Active Learning via Coordinated Matching," Proceedings of the 29th International Conference on Machine Learning, 2012, Edinburgh, Scotland, 8 pages.
Robbins, H., "Some Aspects of the Sequential Design of Experiments," Bulletin of the American Mathematical Society, vol. 58, Sep. 1, 1952, 9 pages.
Minoux, M., "Accelerated greedy algorithms for maximizing submodular set functions," Optimization Techniques, Proceedings of the LNCIS, vol. 7, 1978, 10 pages.
Gittins, J. C., "Bandit Processes and Dynamic Allocation Indices," Journal of the Royal Statistical Society B, vol. 41, No. 2, Jan. 1979, 17 pages.
Guyatt, G. H. et al., "The 6-minute walk: a new measure of exercise capacity in patients with chronic heart failure," Canadian Medical Association Journal, vol. 132, No. 8, Apr. 15, 1985, 5 pages.
Lovely, R. et al., "Effects of Training on the Recovery of Full-Weight-Bearing Stepping in the Adult Spinal Cat," Experimental Neurology, vol. 92, No. 2, May 1986, 15 pages.
Barbeau, H. et al., "Recovery of locomotion after chronic spinalization in the adult cat," Brain Research, vol. 412, No. 1, May 26, 1987, 12 pages.
Colgate, E. et al., "An Analysis of Contact Instability in Terms of Passive Physical Equivalents," Proceedings of the 1989 IEEE International Conference on Robotics and Automation, Scottsdale, Arizona, May 14, 1989, 6 pages.
Wernig, A. et al., "Laufband locomotion with body weight support improved walking in persons with severe spinal cord injuries," Paraplegia, vol. 30, No. 4, Apr. 1992, 10 pages.
Pratt, J. et al., "Series elastic actuators for high fidelity force control," Industrial Robot: An International Journal, vol. 29, No. 3, Available as Early as Jan. 1, 2002, 13 pages.
Winter, D. A. et al., "An integrated EMG/biomechanical model of upper body balance and posture during human gait," Progress in Brain Research, vol. 97, Ch. 32, Available as Early as Jan. 1, 1993, 9 pages.
Pratt, G. et al., "Stiffness Isn't Everything," Proceedings of the Fourth International Symposium on Experimental Robotics, Jun. 30, 1995, Stanford, California, 6 pages.
Basso, D. et al., "MASCIS Evaluation of Open Field Locomotor Scores: Effects of Experience and Teamwork on Reliability," Journal of Neurotrauma, vol. 13, No. 7, Jul. 1996, 17 pages.
Harkema, S. et al., "Human Lumbosacral Spinal Cord Interprets Loading During Stepping," Journal of Neurophysiology, vol. 77, No. 2, Feb. 1, 1997, 15 pages.
Brosamle, C. et al., "Cells of Origin, Course, and Termination Patterns of the Ventral, Uncrossed Component of the Mature Rat

(56) References Cited

OTHER PUBLICATIONS

Corticospinal Tract," The Journal of Comparative Neurology, vol. 386, No. 2, Sep. 22, 1997, 11 pages.
Jones, D. R. et al., "Efficient Global Optimization of Expensive Black-Box Functions," Journal of Global Optimization, vol. 13, 1998, 38 pages.
Dimitrijevic, M. M. et al., "Evidence for a Spinal Central Pattern Generator in Humans," Annals New York Academy Sciences, vol. 860, 1998, 17 pages.
Kakulas, B., "A Review of the Neuropathology of Human Spinal Cord Injury with Emphasis on Special Features," Proceedings of the Donald Munro Memorial Lecture at the American Paraplegia Society 44th Annual Conference, Sep. 9, 1998, Las Vegas, Nevada, 6 pages.
Hashtrudi-Zaad, K. et al., "On the Use of Local Force Feedback for Transparent Teleoperation," Proceedings of the 1999 IEEE International Conference on Robotics and Automation, May 10, 1999, Detroit, Michigan, 7 pages.
Kirkwood, P., "Neuronal Control of Locomotion: From Mollusk to Man—G.N. Orlovsky, T.G. Deliagina and S. Grillner, Oxford University Press," Clinical Neurophysiology, vol. 111, No. 8, Published Online Jul. 17, 2000, Aug. 1, 2000, 2 pages.
Murg, M. et al., "Epidural electric stimulation of posterior structures of the human lumbar spinal cord: 1. Muscle twitches—a functional method to define the site of stimulation." Spinal Cord, vol. 38, 2000, 9 pages.
Auer, P. et al., "Finite-time Analysis of the Multiarmed Bandit Problem," Machine Learning, vol. 47, No. 2, 2002, 22 pages.
Auer, P. "Using Confidence Bounds for Exploitation-Exploration Trade-offs," Journal of Machine Learning Research, vol. 3, 2002, 26 pages.
Dimitrijevic, M. et al., "Clinical Elements for the Neuromuscular Stimulation and Functional Electrical Stimulation protocols in the Practice of Neurorehabilitation," Artificial Organs, vol. 26, No. 3, 2002, 4 pages.
Gerasimenko, Y. et al., "Control of Locomotor Activity in Humans and Animals in the Absence of Supraspinal Influences," Neuroscience and Behavioral Physiology, vol. 32, No. 4, 2002, 7 pages.
Herman, R. et al., "Spinal cord stimulation facilitates functional walking in a chronic, incomplete spinal cord injured," Spinal Cord, vol. 40, No. 2, 2002, 4 pages.
Yakovenko, S. et al., "Spatiotemporal Activation of Lumbosacral Motoneurons in the Locomotor Step Cycle," Journal of Neurophysiology, vol. 87, No. 3, Mar. 2002, 12 pages.
Ivanenko, Y. P. et al., "Temporal Components of the Motor Patterns Expressed by the Human Spinal Cord Reflect Foot Kinematics," Journal of Neurophysiology, vol. 90, No. 5, Nov. 2003, Published Online Jul. 9, 2003, 11 pages.
Steward, O. et al., "False Resurrections: Distinguishing Regenerated from Spared Axons in the Injured Central Nervous System," The Journal of Comparative Neurology, vol. 459, No. 1, Apr. 21, 2003, 8 pages.
Pearson, K., "Generating the walking gait: role of sensory feedback," Progress in Brain Research, vol. 143, Chapter 12, Published Online Nov. 28, 2003, 2004, 7 pages.
Rasmussen, C., "Gaussian Processes in Machine Learning", L.N. A.I., vol. 3176, 2003, 9 pages.
Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, Mar. 15, 2004, 11 pages.
Bareyre, F. et al., "The injured spinal cord spontaneously forms a new intraspinal circuit in adult rats," Nature Neuroscience, vol. 7, No. 3, Published Online Feb. 15, 2004, Mar. 2004, 9 pages.
Dimitrijevic, M. et al., "Electrophysiological characteristics of H-reflexes elicited by percutaneous stimulation of the cauda equina," Abstract No. 4927, Proceedings of the 34th Annual Meeting of the Society for Neuroscience, San Diego, California, 2004, 1 page.
Jilge, B. et al., "Initiating extension of the lower limbs in subjects with complete spinal cord injury by epidural lumbar cord stimulation," Experimental Brain Research, vol. 154, 2004, 19 pages.
Ganley, K. et al., "Epidural Spinal Cord Stimulation Improves Locomotor Performance in Low ASIA C, Wheelchair-Dependent, Spinal Cord-Injured Individuals: Insights from Metabolic Response," Topics in Spinal Cord Injury Rehabilitation, vol. 11, No. 2, 2005, 14 pages.
Krause, A. et al., "Near-optimal Nonmyopic Value of Information in Graphical Models," Proceedings of the Twenty-First Conference on Uncertainty in Artificial Intelligence (UAI'05), 2005, Edinburgh, Scotland, 8 pages.
Minassian, K. et al., "Peripheral and central afferent input to the lumbar cord," Biocybemetics and Biomedical Engineering, vol. 25, No. 3, 2005, 19 pages.
Liu, J. et al., "Stimulation of the Parapyramidal Region of the Neonatal Rat Brain Stem Produces Locomotor-Like Activity Involving Spinal 5-HT7 and 5-HT2A Receptors," Journal of Neurophysiology, vol. 94, No. 2, Published Online May 4, 2005, Aug. 1, 2005, 13 pages.
Timozyk, W. et al., "Hindlimb loading determines stepping quantity and quality following spinal cord transection," Brain Research, vol. 1050, No. 1-2, Published Online Jun. 24, 2005, Jul. 19, 2005, 10 pages.
Wernig, A., "Ineffectiveness• of Automated Locomotor Training," Archives of Physical Medicine and Rehabilitation, vol. 86, No. 12, Dec. 2005, 2 pages.
Nessler, J. et al., "A Robotic Device for Studying Rodent Locomotion After Spinal Cord Injury," IEEE Transactions on Neural Systems and Rehabilitation Engineering, vol. 13, No. 4, Dec. 12, 2005, 10 pages.
Rasmussen, C. et al., "Gaussian Processes for Machine Learning," The MIT Press, Cambridge, Massachusetts, 2006, 266 pages.
Pudo, D. et al., "Estimating Intensity Fluctuations in High Repetition Rate Pulse Trains Generated Using the Temporal Talbot Effect," IEEE Photonics Technology Letters, vol. 18, No. 5, Mar. 1, 2006, 3 pages.
Reinkensmeyer, D. et al., "Tools for understanding and optimizing robotic gait training," Journal of Rehabilitation Research & Development, vol. 43, No. 5, Aug. 2006, 14 pages.
Frey, M. et al., "A Novel Mechatronic Body Weight Support System," IEEE Transactions on Neural Systems and Rehabilitation Engineering, vol. 14, No. 3, Sep. 18, 2006, 11 pages.
Kocsis, L. et al. "Bandit Based Monte-Carlo Planning," Proceedings of the European Conference on Machine Learning, Springer, Berlin, Heidelberg, Sep. 2006, 12 pages.

\* cited by examiner

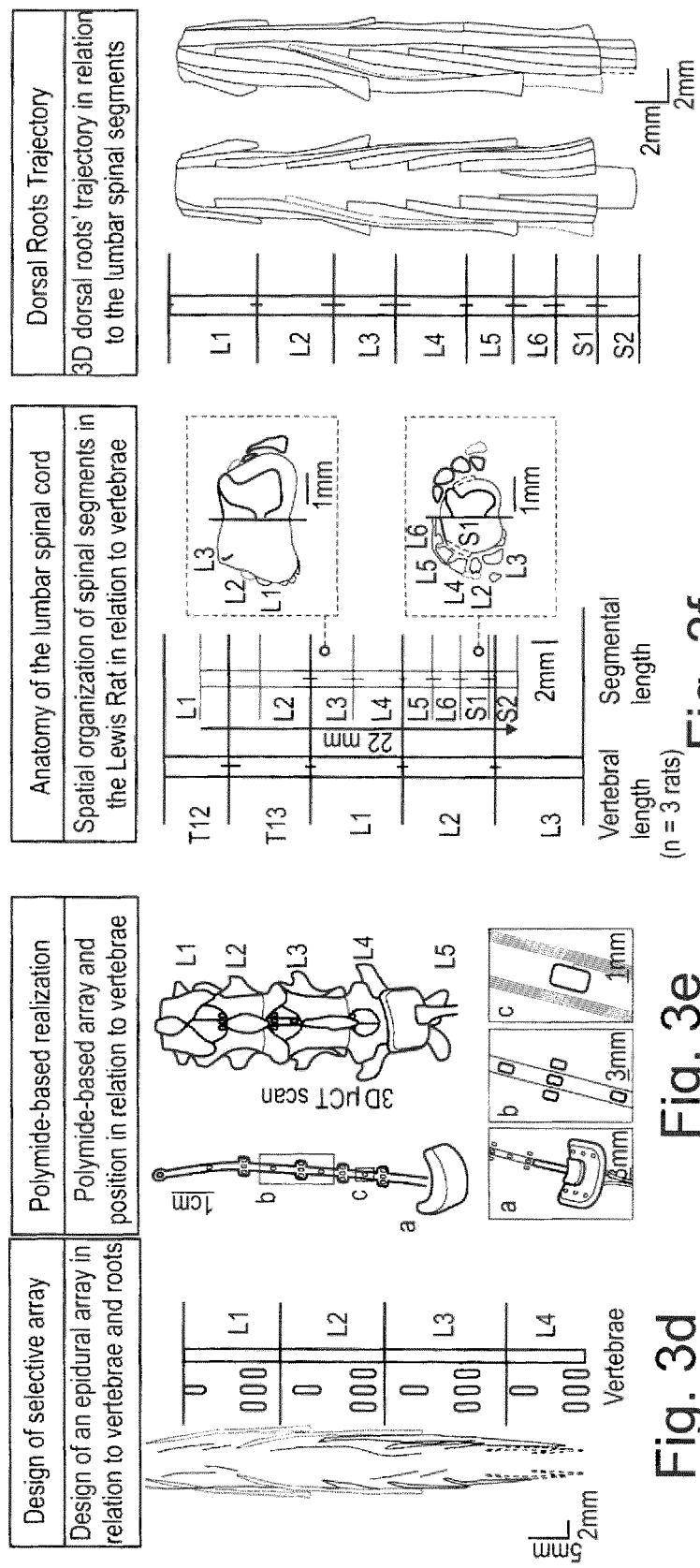

SYSTEM FOR PLANNING AND/OR PROVIDING NEUROMODULATION

CROSS-REFERENCE TO RELATED APPLICATIONS

The present application is a U.S. National Phase of International Application No. PCT/EP2018/082942, entitled "A SYSTEM FOR PLANNING AND/OR PROVIDING NEUROMODULATION", and filed on Nov. 29, 2018. International Application No. PCT/EP2018/082942 claims priority to European Patent Application No. 17205360.5, filed on Dec. 5, 2017. The entire contents of each of the above-listed applications are hereby incorporated by reference for all purposes.

TECHNICAL FIELD

The present invention relates to a system for planning and/or providing neuromodulation, especially neurostimulation.

BACKGROUND AND SUMMARY

Decades of research in physiology have demonstrated that the mammalian spinal cord embeds sensorimotor circuits that produce movement primitives (cf. Bizzi, E., et al., *Modular organization of motor behavior in the frog's spinal cord*. Trends in neurosciences 18, 442-446 (1995); Levine, A. J. et al. *Identification of a cellular node for motor control pathways*. Nature neuroscience 17, 586-593, (2014)). These circuits process sensory information arising from the moving limbs and descending inputs originating from various brain regions in order to produce adaptive motor behaviours.

A spinal cord injury (SCI) interrupts the communication between the spinal cord and supraspinal centres, depriving these sensorimotor circuits from the excitatory and modulatory drives necessary to produce movement.

A series of studies in animal models and humans showed that electrical neuromodulation of the lumbar spinal cord using epidural electrical stimulation (EES) is capable of (re-)activating these circuits. For example, EES has restored coordinated locomotion in animal models of SCI, and isolated leg movements in individuals with motor paralysis (cf. van den Brand R, et al., *Restoring Voluntary Control of Locomotion after Paralyzing Spinal Cord Injury*. Science 336, 1182-1185 (2012); Angeli C A, et al., *Altering spinal cord excitability enables voluntary movements after chronic complete paralysis in humans*. Brain: a journal of neurology 137, 1394-1409 (2014); Harkema S, et al., *Effect of epidural stimulation of the lumbosacral spinal cord on voluntary movement, standing, and assisted stepping after motor complete paraplegia: a case study*. The Lancet 377, 1938-1947; Danner S M, et al., *Human spinal locomotor control is based on flexibly organized burst generators*. Brain: a journal of neurology 138, 577-588 (2015); Courtine G, et al., *Transformation of nonfunctional spinal circuits into functional states after the loss of brain input*. Nature neuroscience 12, 1333-1342, (2009); Capogrosso M, et al., *A brain-spine interface alleviating gait deficits after spinal cord injury in primates*. Nature 539, 284-288, (2016)).

Computational models (cf. Capogrosso M, et al., *A computational model for epidural electrical stimulation of spinal sensorimotor circuits*. The Journal of neuroscience: the official journal of the Society for Neuroscience 33, 19326-19340 (2013); Moraud E M, et al., *Mechanisms Underlying the Neuromodulation of Spinal Circuits for Correcting Gait and Balance Deficits after Spinal Cord Injury*. Neuron 89, 814-828 (2016); Rattay F, et al., *Epidural electrical stimulation of posterior structures of the human lumbosacral cord: 2. quantitative analysis by computer modeling*. Spinal cord 38, 473-489 (2000)) and experimental studies (cf. Gerasimenko Y, et al., *Program No. 447.445* (Soc. Neurosci. Abstr.); Minassian K, et al., *Human lumbar cord circuitries can be activated by extrinsic tonic input to generate locomotor-like activity*. Human Movement Science 26, 275-295 (2007)) have provided evidence suggesting that EES recruits large-diameter sensory afferents, especially proprioceptive circuits (cf. Moraud E M, et al., *Mechanisms Underlying the Neuromodulation of Spinal Circuits for Correcting Gait and Balance Deficits after Spinal Cord Injury*. Neuron 89, 814-828, (2016)).

Consequently, the stimulation leads to the activation of motoneurons through mono- and polysynaptic proprioceptive circuits, as well as increases the general excitability of the lumbar spinal cord. In addition, the natural modulation of proprioceptive circuits during movement execution gates the effects of EES towards functionally relevant spinal pathways. Concretely, due to phase-dependent modulation of proprioceptive circuits, the effects of stimulation are restricted to specific ensembles of leg motoneurons that are coherent with the phase of the movement (cf. Moraud E M, et al., *Mechanisms Underlying the Neuromodulation of Spinal Circuits for Correcting Gait and Balance Deficits after Spinal Cord Injury*. Neuron 89, 814-828 (2016)).

Moreover, since EES engages motoneurons through trans-synaptic mechanisms, residual inputs from supraspinal centres are also capable of gating the effects of EES towards specific circuits or increasing the excitability of the motoneuron pools (and thus their responsiveness to EES) in order to mediate voluntary modulation of leg movements (cf. van den Brand R, et al., Restoring Voluntary Control of Locomotion after Paralyzing Spinal Cord Injury. Science 336, 1182-1185 (2012); Angeli C A, et al., Altering spinal cord excitability enables voluntary movements after chronic complete paralysis in humans. Brain: a journal of neurology 137, 1394-1409 (2014); Harkema, S, et al. Effect of epidural stimulation of the lumbosacral spinal cord on voluntary movement, standing, and assisted stepping after motor complete paraplegia: a case study. The Lancet 377, 1938-1947).

This conceptual framework was exploited to design a neuromodulation strategy that targets specific ensembles of proprioceptive afferents associated with flexion and extension of both legs (cf. Bizzi E, et al., *Modular organization of motor behavior in the frog's spinal cord*. Trends in neurosciences 18, 442-446 (1995); Levine A J, et al. *Identification of a cellular node for motor control pathways*. Nature neuroscience 17, 586-593 (2014)).

This strategy, termed spatiotemporal neuromodulation, consists of delivering EES bursts through targeted electrode configurations with a temporal structure that reproduces the natural activation of leg motoneurons during locomotion. This spatiotemporal neuromodulation therapy reversed leg paralysis in both rodent and primate models of SCI (cf. Capogrosso M, et al., *A brain-spine interface alleviating gait deficits after spinal cord injury in primates*. Nature 539, 284-288, (2016); Wenger N, et al., *Spatiotemporal neuromodulation therapies engaging muscle synergies improve motor control after spinal cord injury*. Nat Med 22, 138-145 (2016)).

This conceptual framework is applicable to develop spatiotemporal neuromodulation therapies for enabling leg motor control in humans with SCI.

Generally speaking, known stimulation systems use either Central Nerve System (CNS) stimulation, especially Epidural Electrical Stimulation (EES), or Peripheral Nerve System (PNS) Stimulation, especially Functional Electrical Stimulation (FES).

Epidural Electrical Stimulation (EES) is known to restore motor control in animal and human models and has more particularly been shown to restore locomotion after spinal cord injury by artificially activating the neural networks responsible for locomotion below the spinal cord lesion (cf. Capogrosso M, et al., *A Computational Model for Epidural Electrical Stimulation of Spinal Sensorimotor Circuits, Journal of Neuroscience* 4 Dec. 2013, 33 (49) 19326-19340; Courtine G, et al., *Transformation of nonfunctional spinal circuits into functional states after the loss of brain input, Nat Neurosci.* 2009 October; 12(10): 1333-1342; Moraud E M, et al, *Mechanisms Underlying the Neuromodulation of Spinal Circuits for Correcting Gait and Balance Deficits after Spinal Cord Injury, Neuron Volume* 89, Issue 4, p 814-828, 17 Feb. 2016). EES does not directly stimulate motor-neurons but the afferent sensory neurons prior to entering into the spinal cord. In this way, the spinal networks responsible for locomotion are recruited indirectly via those afferents, restoring globally the locomotion movement by activating the required muscle synergies. The produced movement is functional; however, due to relatively poor selectivity (network activation instead of selective targeting of key muscles) the controllability is low and the imprecisions hinder fluidity and full functionality in the potential space of the movement.

Peripheral Nerve System (PNS) Stimulation systems used to date in the clinic are known as Functional Electrical Stimulation (FES) that provides electrical stimulation to target muscles with surface electrodes, either directly through stimulation of their motorfibers (neuro-muscular stimulation), or through a limited set reflexes (practically limited to the withdrawal reflex) or by transcutaneously stimulating the peripheral nerves. The resulting muscle fatigue has rendered FES unsuitable for use in daily life. Furthermore, successes have remained limited through cumbersome setups when using surface muscle stimulation, unmet needs in terms of selectivity (when using transcutaneous nerve stimulation) and a lack of stability (impossible to reproduce exact electrode placement on a daily basis when stimulating muscles, moving electrodes due to clothes, sweating).

US 2016/030750 A1 discloses a computer implemented system and method facilitates the generation, sharing and refinement of volumes to stimulate anatomical tissue, such as spinal cord stimulation. The computer system analyses the volumes as well. More specifically, a computer implemented system and method facilitates a cycle of generation, sharing, and refinement of volumes related to stimulation of anatomical tissue, such as brain or spinal cord stimulation. Such volumes can include target stimulation volumes, side effect volumes, and volumes of estimated activation. A computer system and method also facilitates analysis of groups of volumes, including analysis of differences and/or commonalities between different groups of volumes.

US 2016/001096 A1 describes methods and systems that use multiple therapeutic modalities to cause deep or superficial deep-brain stimulation. Methods for treatment of clinical conditions and physiological impacts are described, as well as methods for Guided Feedback control of non-invasive deep brain or superficial neuromodulator, as well as the non-invasive neuromodulation of the spinal cord by ultrasound energy.

EP 2 810 689 A1 and EP 2 810 690 A1 describe a system for planning and providing a therapy for Deep Brain neural applications, especially neurostimulation and/or neurorecording with at least one lead with a plurality of electrodes. The invention concerns a method for focusing the stimulation field provided by an active contact of a lead.

US 2015/066111 A1 discloses a tool for assisting in the planning or performing of electrical neuromodulation of a patient's spinal cord by calculating a volume of activation, registering electrodes and their position.

Current systems for neuromodulation in the field of the treatment of spinal cord injuries (SCI), for example after trauma or stroke or illness, have to match each input signal to a specific reaction of the patient. This can be quite time-consuming and also exhaustive for the patient to be treated and also for the physician and medical support staff. This object is solved according to the present invention by a system for planning and/or providing neuromodulation according to the subject matter of claim 1. Accordingly, a system for planning and/or providing neuromodulation is provided, especially for neuro stimulation, comprising:

a stimulation related basic data storage module for storing the stimulation related basic data, a stimulation related response data storage module for storing the stimulation related response data, transfer module configured and arranged such that the stimulation related basic data received by the data input module are linked and/or translated into and/or with the response data or artificial response data created by the transfer module, wherein the data generated by the transfer module are transfer data, the transfer data comprising link data and/or translation data and/or artificial response data, a transfer response data storage module for storing the transfer data, mapping module configured and arranged such that based on the stimulation related basic data and stimulation related response data and the transfer data a digital characteristic map is generated, which describes the interrelation between the stimulation related basic data and the stimulation related response data and the transfer data, and analysis module configured and arranged such that the digital characteristic map can be analyzed automatically.

The invention is based on the basic idea that the multidimensional relationship between the stimulation signal and the patient response shall be described by a digital characteristic map, which forms a kind of functional mapping. This functional mapping describes inter alia the relationship in a specific situation at a specific point of time of stimulation input provided and the respective resulting output, which is for example a patient response e.g. in form of movement. In other words, the connection and transformation of a specific input signal, i.e. a stimulation input, and the respective output signal, i.e. the reaction and/or movement of the subject/patient is compiled and the respective data are collected. Then, these data describe as a kind of multidimensional map the respective reaction of the patient of specific input at a specific point of time. Such specific input at a specific point of time can be for example the above-mentioned spatiotemporal stimulation. By creating and establishing the multidimensional map spatiotemporal stimulation input and the respective output, i.e. the respective patient reaction, a spatiotemporal stimulation can be configured for specific scenarios related to specific movements of or tasks to be performed by the patient like sitting, standing up (sit to stand), standing, walking, climbing stairs, stop walking, stand to sit. So, by using the multidimensional map in connection with spatiotemporal stimulation protocols can be created and provided, which are directly translatable to the design of spatiotemporal neuromodulation therapies to reverse inter alia leg paralysis. The digital characteristic map may be a curve, a plurality of curves or a landscape, e.g. a three-dimensional or even multi-dimensional landscape of a plurality of curves, which describe the dependencies between one specific input and one specific output at a certain point of time a pre-defined position. So, it is also possible that the landscape is changing its shape in dependency over the time.

In connection with the system specific kind of data are used.

In particular, there are stimulation related basic data. The stimulation related basic data are data that describe the stimulation in greater detail, in particular which kind of stimulation, which elements used for the stimulation and also the characteristics of a patient receiving the stimulation is present and/or used. Thus, the stimulation related basic data may define parameters of a neurostimulation system for treating a patient.

Moreover, there are stimulation related response data. The stimulation related response data describe, what kind of response is received in connection with the stimulation. In particular, these kind of data describe results of any kind triggered and received as response by the provided stimulation. Such stimulation related response data may include (but are not limited to) data describing activation of the spinal cord as response to the stimulation or specific movements and/or reactions of the patient induces by the neurostimulation. The stimulation related response data may inter alia comprise data of the activation of the spinal cord as response to the stimulation.

Also, there are transfer data. The transfer data are building a bridge between the stimulation related basic data and the stimulation related response data. There may be link data and/or translation data or a artificial response data, which may fill gaps, where no direct link between an input and an output is given. In particular artificial response data might be for example but not limited to extrapolation data or calculated data. The transfer data may comprise artificial response data and/or link data and/or translation data, which link and/or translate at least partially the stimulation related basic data and the stimulation related response data with each other.

The invention can also be used in the context of neuromodulation, especially neurostimulation, where the electrical stimulation parameters defining the stimulation for the subject to be treated can vary cyclically over time in a pre-programmed manner, i.e. one cycle with pre-defined timings for the various stimulation patterns is repeated over and over again.

Such neuromodulation approaches may cover (but are not limited to) invasive or non-invasive or mixed approaches. They may be based on neurostimulation only. Also, pharmacological approaches or the like shall be covered and understood by the term neuromodulation. Neurostimulation may be applied epidurally and/or subdurally and/or transcutaneously or in another suitable manner.

The use of pre-programmed temporal stimulation pattern data together with the use of pre-programmed spatial stimulation pattern data allow a stimulation at the correct place at the correct time to facilitate, enable or trigger the intended action of the subject. Such an action can be movement of extremities like feet and/or legs and/or arms, contraction and/or relaxation and/or any movement of muscles in connection with movement of the subject or cardiovascular functions of the subject, e.g. blood pressure control and/or blood circulation support and/or blood circulation control. Such an approach can be characterized as open-loop phasic stimulation. Basically, it forms a way to stimulate physically the nervous system, especially the spinal cord of a subject or patient without the need for complex and/or complicated feedback systems. It can easily be implemented to promote locomotion, cyclical activity with physical training devices and reduce orthostatic hypotension, after nervous system impairments such as spinal cord injury. So it is possible to improve a neuromodulation system, e.g. in the field of improving recovery after neurological disorders like spinal cord injury (SCI), for example after trauma or stroke or illness, especially in that neuromodulation and/or neurostimulation can be provided in almost any environment and in daily life, adapted to the patient's needs and providing the needed assistance in training and daily life for the patient, also adjusted to the progress of the rehabilitation of the patient.

The mapping module may be configured and arranged such that the digital characteristic map is generated automatically. By generating the digital characteristic map automatically a very efficient and time-consuming procedure as now in the state of the art may be overcome. The dependencies between input and output can be generated faster and more efficient. The automatic generation process may contain steps like interpolation or the use of plausible assumptions based on known biophysical or physiological relations. There may be an algorithm that uses iterations to find the most suitable way to describe at least parts of the digital characteristic map.

Furthermore, the stimulation related basic data may comprise at least one selected from
electrode data, and/or
stimulation characteristic data, and/or
patient data, and/or
stimulation data, and/or
treatment application data.

These kind of data and/or parameters describe in a very clear and well-defined way the circumstances and variables of the stimulation to be provided or the provided stimulation. With this kind of data the input situation in dependency of the time can be described. Generally, further parameters may also be used independently, alternatively or additionally.

Additionally, the stimulation related response data may comprise data comprise at least one selected from
sequence of events data, and/or
motion data, and/or
EMG data, and/or
afferent signal data, and/or
efferent signal data, and/or
impedance data, and/or
EEG data, and/or
BCI data.

This kind of data and/or parameters describe in a very clear and well-defined way the circumstances and variables of the result or output caused by the stimulation to be provided or the provided stimulation. With this kind of data the output situation in dependency of the time can be described. Generally, further parameters may also be used independently, alternatively or additionally.

Also, the transfer module may be configured and arranged such that at least one kind of data selected from
body posture data, and/or
static and/or dynamic data, and/or task and/or activity data, and/or
time and/or delay data, and/or
rehabilitation data, and/or
drug treatment data, and/or
data related to the voluntariness of movement,
is or are used to generate the transfer data.

The transfer data may be used to prepare the relationship between the stimulation related basic data and the stimulation related response data. The transfer data may also be used to fill gaps, where there is no pair between stimulation related basic data and stimulation related response data.

In particular, where there is no matching stimulated related response data to specific stimulation related basic data, by means of the transfer data, stimulation related response data may be calculated and vise versa. On the basis of the stimulation related basic data, the stimulation related response data and the transfer data, a fully fletched picture of the interrelationship between stimulation related basic data and stimulation related response data may be created. This kind of picture or mapping consists of real data and also for example calculated and/or virtual data.

The virtual mapping module allows to directly generate the digital characteristic map virtually online, which is enhancing the process of mapping the stimulation related basic data and the stimulation related response data.

Furthermore, the analysis module may be configured and arranged such that onset points within the digital characteristic map are identified automatically. Such onset points define points and stimulation settings and the respective output, where a value is reached, which creates on a specific input a specific output. The existence of onset points has been realized in connection with this invention, as specific setups and input parameters do not create any response and it is necessary to reach and go beyond an onset point to receive a specific output.

Furthermore, the analysis module may be configured and arranged such that saturation points within the digital characteristic map are identified automatically. Such saturation points are points, where upon increasing input signals no further output may be achieved. The knowledge about such saturation points in connection with other details of the digital characteristic map will be helpful to use the neurostimulation provided very efficiently.

The analysis module may be configured and arranged such that specificity points within the digital characteristic map are identified automatically. Such a specificity point may be located between a onset point and a saturation point and define the optimal point with no interference with other effects that may happen upon stimulation.

Furthermore, the system may further comprise a visualization module. Such a visualization module may at least comprise a display or any other output module, for example loudspeakers, beamer, projectors of any kind or the like. With the visualization module information may be output to a user and visualized.

The visualization module may be configured and arranged such that at least partially stimulation related basic data and at least partially stimulation related response data may be displayed.

The visualization module may be configured and arranged such that the stimulation related response data may be visualized at least schematically with representations of muscles or muscles groups receiving neurostimulation. For example, schematically representations of the muscle groups in connection with the outlines of the human body may be displayed and activated/stimulated muscle groups may be displayed with another color then unstimulated muscle groups.

The system may comprise stimulation related response data input elements and the system may be configured and arranged such that an inverse control is provided by inputting stimulation related response data via the stimulation related response data input elements and that the system further comprises selection elements, which are configured and arranged such that based on the digital characteristic functional map suitable stimulation related basic data may be selected. The input elements may be for example a touchscreen, input elements of a computer like a keyboard or a mouse or a touchpad or the like. By inverse control the user may be for example select the muscle groups to be stimulated and then the respective stimulation settings may be automatically provided by the system.

Furthermore, the system may comprise a neuromodulation settings generation module, which is configured and arranged to translate the digital characteristic functional map into neuromodulation parameter settings for a neuromodulation treatment of a subject. Here, a result based planning may be done, i.e. by selecting the respective results and the stimulation result achieved, the necessary parameter settings may be selected automatically by the system. In other words, by defining the desired output, the necessary input data will be found by the system.

The neuromodulation settings generation module may comprise a transfer interface, which is configured and arranged for transferring neuromodulation parameter settings from the system to a neuromodulation device. Such a neuromodulation device may be for example an implanted neurostimulator. There may be for example a transcutaneous transfer interface, for example a wireless transfer system by using RF-technology, inductance, ultrasound or the like.

BRIEF DESCRIPTION OF THE FIGURES

Further details and advantages of the present invention shall now be disclosed in connection with the drawings.
It is shown in
FIG. 1 a schematical overview of a possible embodiment for a system for planning and/or providing neuromodulation.

DETAILED DESCRIPTION

Figure 1:
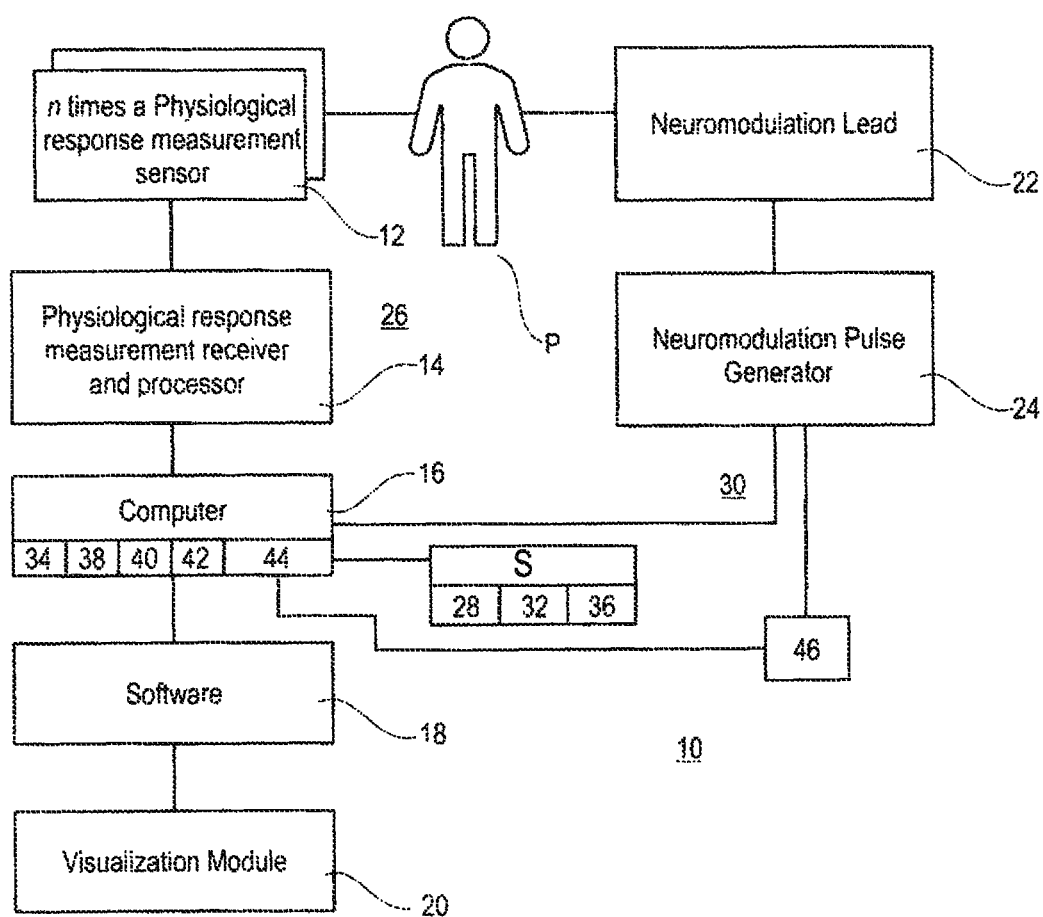

FIG. 1 shows as schematical overview of a possible embodiment for a system for planning and/or providing neuromodulation, here neurostimulation according to the present invention.

The patient P is connected to the system 10.

The system 10 comprises at least:
- a physiological response measurement sensor 12
- a physiological response measurement receiver and processor 14
- a computer 16
- a software 18
- a visualization module 20
- a neuromodulation lead 22 and neuromodulation pulse generator 24.

The physiological response measurement sensor 12 and the physiological response measurement receiver processor 14 function as a first data input module 26 for stimulation related basic data.

The computer 16 and the software 18 are connected to a storage being part of the computer 16.

The storage S comprises a stimulation related basic data storage module 28 for storing the stimulation related basic data obtained by the first data input module 26 for stimulation related basic data.

The stimulation related basic data may comprise at least one (or more or all) selected from
- electrode data, and/or
- stimulation characteristic data, and/or
- patient data, and/or
- stimulation data, and/or
- treatment application data.

In the shown embodiment, the neuromodulation lead 22, the neuromodulation pulse generator 24, the physiological response measurement sensor 12 and the physiological response measurement receiver and processor 14 form also a second data input module 30 for stimulated related response data.

The stimulation related response data are stored in a further stimulation related response data storage module 32, which is also part of the storage S.

The stimulation related response data comprise data comprise at least one (or more or all) selected from
- sequence of events data, and/or
- motion data, and/or
- EMG (electromyography) data, and/or
- afferent signal data, and/or
- efferent signal data, and/or
- impedance data, and/or
- EEG (electroencephalograhy) data, and/or
- BCI (brain control interface) data.

Moreover, the computer 16 comprises a transfer module 34.

The transfer module 34 is configured and arranged such that the stimulation related basic data received by the data input module are linked and/or translated into and/or with the response data and/or artificial response data created by the transfer module 34, wherein the data generated by the transfer module 34 are transfer data, the transfer data comprising link data and/or translation data and/or artificial response data.

The transfer module 34 may configured and arranged such that at least one kind of data selected from
- body posture data, and/or
- static and/or dynamic data, and/or
- task and/or activity data, and/or
- time and/or delay data, and/or
- rehabilitation data, and/or
- drug treatment data, and/or
- data related to the voluntariness of movement, is or are used to generate the transfer data.

Moreover, there is a transfer response data storage module for storing the transfer data, which is also part of the storage S.

Furthermore, the computer 16 comprises for creating a digital characteristic map 36 a mapping module 38.

The mapping module 38 is configured and arranged such that based on the stimulation related basic data and the stimulation related response data and the transfer data digital characteristic map 36 is generated, which describes the interrelation between the stimulation related basic data and the stimulation related response data and the transfer data.

The mapping module 38 may be configured and arranged such that the digital characteristic map 36 is generated automatically.

The system 10 may further comprise a virtual mapping module 40, which is configured and arranged to generate the digital characteristic map virtually online.

Moreover, the system 10 comprises a correlation and/or simulation module 42, which is configured and arranged to correlate on the basis of digital characteristic map by way of simulation the stimulation related basic data and the stimulation related response data and the transfer data.

The correlation and/or simulation module 42 also has the functionality of an analysis module or is embodied as analysis module 42. The analysis module can be also embodied as a separate module or element.

The correlation and/or simulation module is configured and arranged such that from a preselected stimulation related basic data the correlating stimulation related response data are identified. Also, from a preselected stimulation related response data the correlating stimulation related basic data may be identified.

The system 10 further comprises a neuromodulation settings generation module 44, which is configured and arranged to translate the digital characteristic map into neuromodulation parameter settings for a neuromodulation treatment of a subject.

Furthermore, the neuromodulation settings generation module 44 comprises a transfer interface 46, which is configured and arranged for transferring neuromodulation parameter settings from the system to a neuromodulation device, here the Neuromodulation Pulse Generator 24.

The analysis module 42 is configured and arranged such that the digital characteristic map can be analyzed automatically.

Moreover, the analysis module 42 is configured and arranged such that onset points within the digital characteristic map are identified automatically.

Also, the analysis module 42 is configured and arranged such that saturation points within the digital characteristic map are identified automatically.

Additionally, the analysis module 42 is configured and arranged such that specificity points within the digital characteristic map are identified automatically.

The system 10 further comprises a visualization module 20.

The visualization module 20 is configured and arranged such that at least partially stimulation related basic data and at least partially stimulation related response data are displayed.

The visualization module 20 is configured and arranged such that stimulation related response data are visualized at least schematically with representations of muscles or muscles group receiving neurostimulation.

The system comprises stimulation related response data input module and that the system is configured and arranged such that an inverse control is provided by inputting stimulation related response data via the stimulation related response data input module and that system further comprises selection module, which are configured and arranged such that based on the digital characteristic map suitable stimulation related basic data are selected.

Also, the system 10 comprises a neuromodulation settings generation module, which is configured and arranged to translate the digital characteristic map into neuromodulation parameter settings for a neuromodulation treatment of a subject.

The above system and process may be also set up as a self-learning or machine-learning process. Especially all kind of maps may be generated in a self-learning or machine-learning process.

Figure 2:
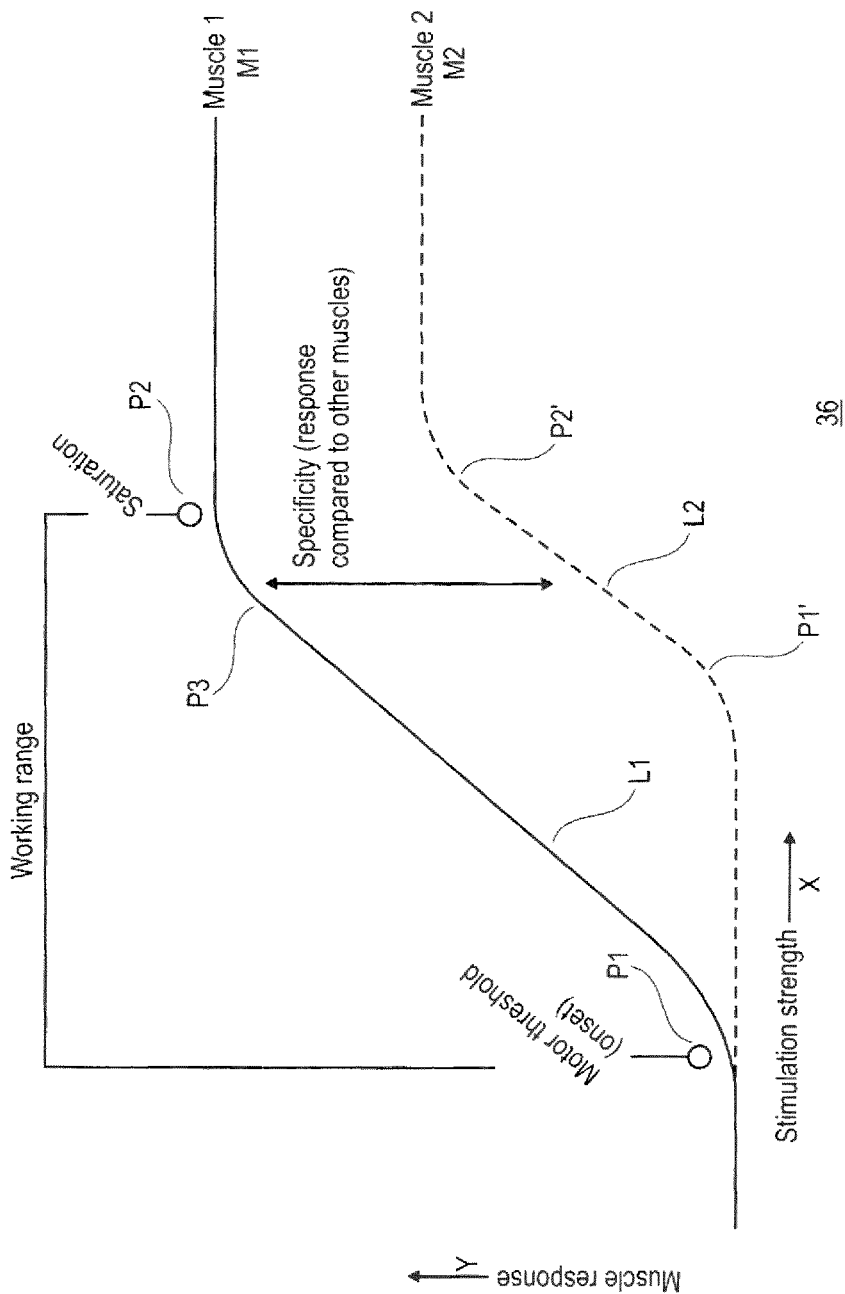
FIG. 2 a (two-dimensional/2D) part of the obtained digital characteristic map.

FIG. 2 shows in 2D a part of the obtained digital characteristic map 36, describing the interrelation between the stimulation related basic data and the stimulation related response data and the transfer data.

On the x-axis the stimulation strength is shown.

On the y-axis the muscle response is shown.

In the digital characteristic map 36, two lines L1 and L2 describing the connection between the stimulation strength (i.e. stimulation related basic data) with the muscle response (stimulation related response data), wherein the connection can be seen as kind of a transfer function (i.e. stimulation related transfer data).

The first line L1 is describing the stimulation response of a first muscle M1 and the dashed line L2 is describing the stimulation response for a second muscle M2.

As can be seen, at a point of stimulation P1 muscle M1 starts to react.

This point P1 is called motor threshold point or onset point.

At this point P1, muscle M2 shows no reaction.

Increasing the stimulation strength will result at some point in a saturation, this point being denoted as point P2, also called saturation point P2.

This point P2, being the saturation point is defining the point at which no further stimulation will receive in stronger muscle activity of muscle M1.

Thus, this point is called saturation point, as increasing the stimulation will not result in better stimulation results and muscle activity.

As can be seen, at point P1' a second muscle starts to react on the applied stimulation, however, at a lower level and with less activity. So, a specificity point P3 may be defined.

The specificity point P3 defines a point, where muscle M1 shows relatively high response, whereas the response of muscle M2, which is also stimulated by the applied stimulation shows less activity, which is still at a level that can be accepted, as it is not really relevant.

Also shown is the saturation point P2' for muscle M2.

FIG. 2 shows a part of digital characteristic map for example for a specific subset of electrodes of an electrode array that is placed in the vicinity of the spinal cord, for example to perform epidural electrical stimulation (EES). By already knowing the connection the placement of the electrodes vis-a-vis the spinal cord and the afferent sensory neurons, the necessary muscles or muscle groups needed for a specific movement can be addressed.

When generating the digital characteristic map, the user is confronted with a plurality of degrees of freedom.

Moreover, fast scans are limited by the response time of the muscles (approx. 2 s/0.5 hz).

This will lead to long mapping times for generating the digital characteristic map.

Thus, here optimization might be wanted.

This can be done by optimizing the patients specific mapping procedure, i.e. finding the optimal stimulation settings for a given task.

Therefore, the following options can be used alternatively or in combination:

By applying specific search function instead of a current step-wise approach, the time consuming step-wise approach can be avoided. Possible approaches in connection with this search function approach are particle swarm, genetic, steepest gradient, optimization algorithms.

A model fitting approach may be used. Here, a patient specific or generic model or the like may be used that predicts muscle response for a specific stimulation and uses the actual mapping to fine-tune and/or register and/or adapt this model to the individual/specific patient.

There may be a data base of patients. Here iterative/machine learning methods may be used for mappings from previous patients to suggest (patient-specific) stimulation settings, probabilistic/statistics can be used, e.g. if one use those settings, then the probability of an effective stimulation may be a certain percentage X % and the crosstalk may be another certain percentage Y %.

For the above three methods, certain quality indicators/optimization object functions may be used such as sensitivity index, cross-talk, muscle onset, muscle saturation or the like.

The above three approaches may improve the generation of the digital characteristic map (the so called mapping procedure) by:

reducing the mapping times creating patient specific optimum results potential reduction of the number of EMG's required, making the procedure easier and faster theoretically one can abandon the use of EMG's at all by fine-tuning of the used motion sensors.

FIG. 3a-i, and k show several details of the anatomical structures to be stimulated and anatomical structures of interest.

FIG. 3a-e relates to the example of Rhesus monkeys.

FIG. 3f-i, and k relate to rodents, here Louis rats.

Figure 3A:
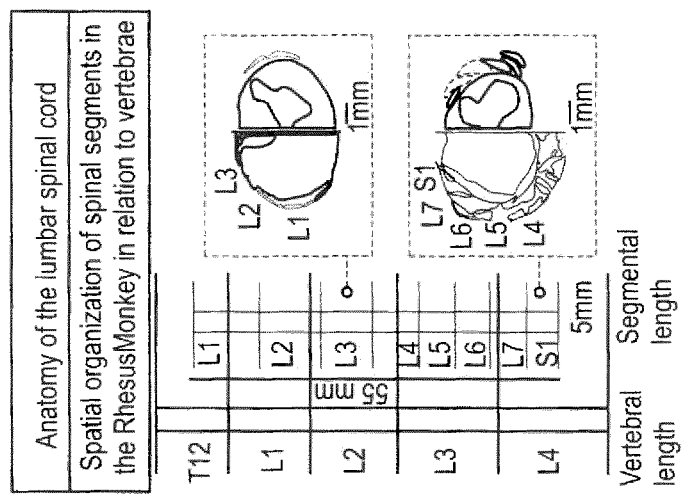
FIG. 3a-i, and k several details of the anatomical structures to be stimulated and anatomical structures of interest.

FIG. 3a shows the anatomy of the lumbar spinal cord of a Rhesus monkey to be stimulated.

Here this spatial organization of spinal segments of the Rhesus monkey in relation to the vertebrae is shown.

Figure 3B:
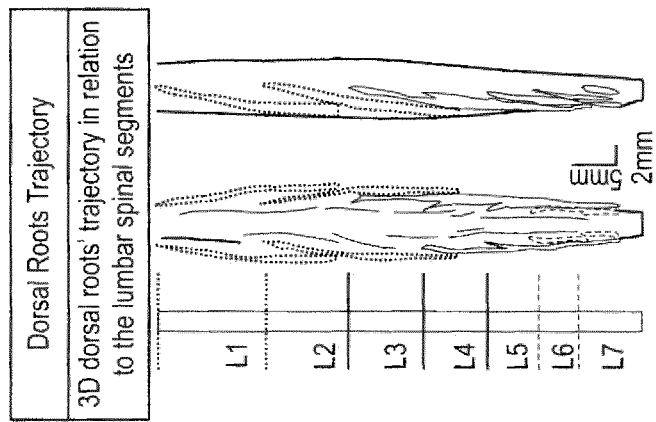

FIG. 3b shows the dorsal roots trajectory.

Here the 3D-dorsal roots' trajectory in relation to the lumbar spinal segment is shown.

Figure 3C:
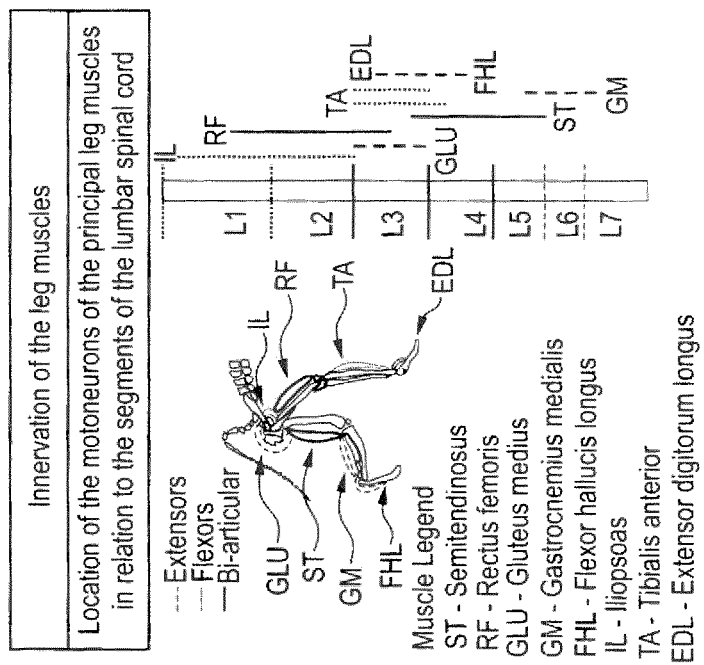

FIG. 3c shows the innervation of leg muscles, in particular the location of the motor neurons of the principle leg muscles in relation to the segments of the lumbar spinal cord.

Shown are extensor muscles with the denotation EXT, flexor muscles with the reference sign FLEX and the articular muscles with the reference sign B.

The muscles are denoted as follows:

ST—SEMITENDINOSUS
RF—RECTUS FEMORIS
GLU—GLUTEUS MEDIUS
GM—GASTROCNEMIUS MEDIALES
FHL—FLEXOR HALLUCIS LONGUS
IL—ILIOPSOAS
TA—TIBIALIS ANTERIOR
EDL—EXTENSOR DIGITORUM LONGUS.

FIG. 3d shows the design of a selective array of electrodes of for example a neuromodulation lead 22.

Here, the design of an epidural array in relation to the vertebrae and roots of the spinal cord is shown.

FIG. 3e shows a polyamide-based realization.

Here, the polyamide-based array and position in relation to the vertebrae is shown.

FIG. 3f-i, and k show respectively the corresponding drawings for rodents, here Lewis rats.

In particular, it is shown in

Figure 3K:
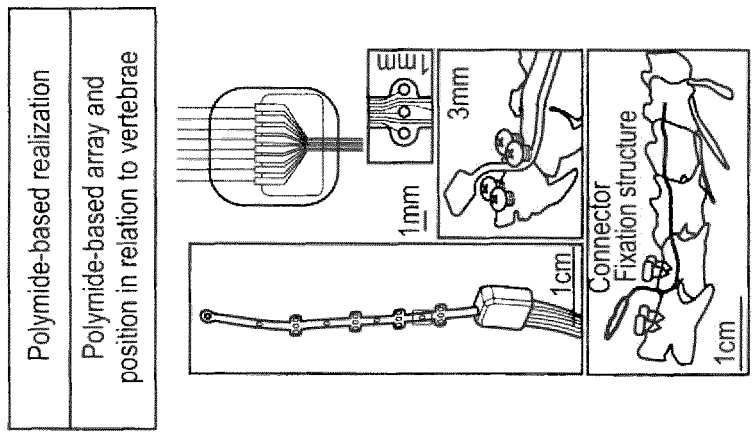
Figure 3I:
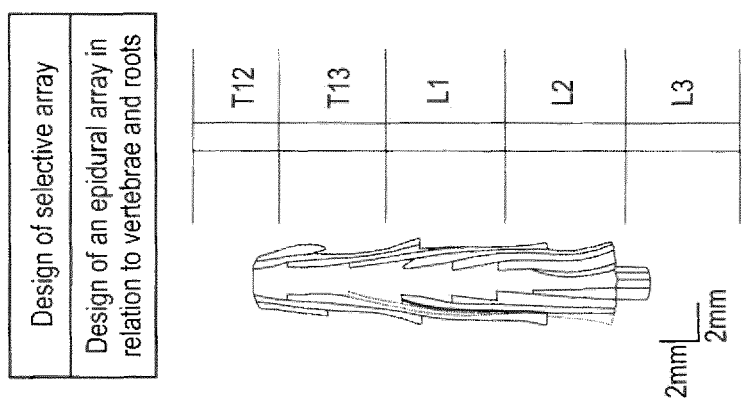
Figure 3H:
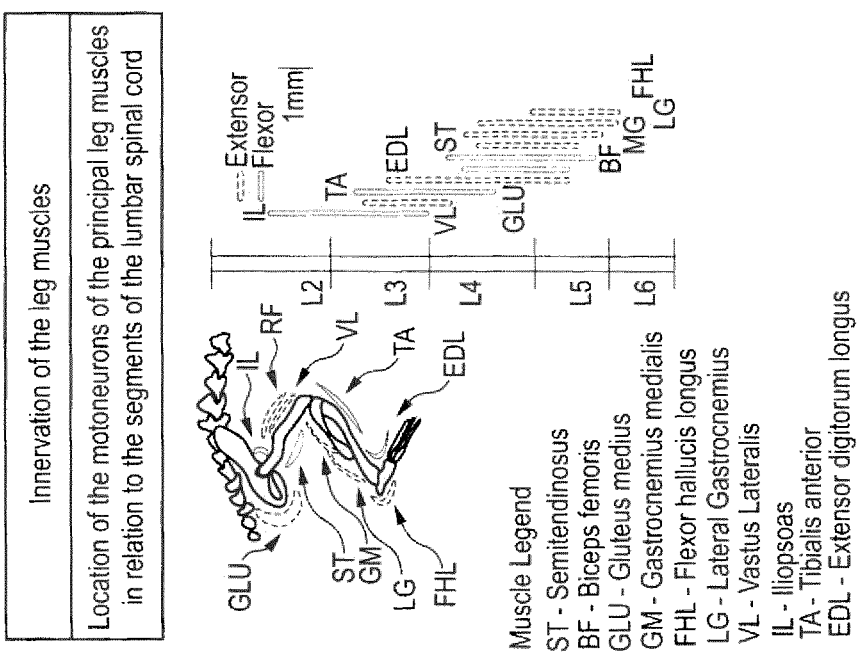

FIG. 3f the anatomy of the lumbar spinal cord of a rodent,

FIG. 3g the dorsal roots trajectory,

FIG. 3h the innervation of the leg muscles,

FIG. 3i the design of the selective array, and

FIG. 3k the polyamide-based realization.

Figure 4:
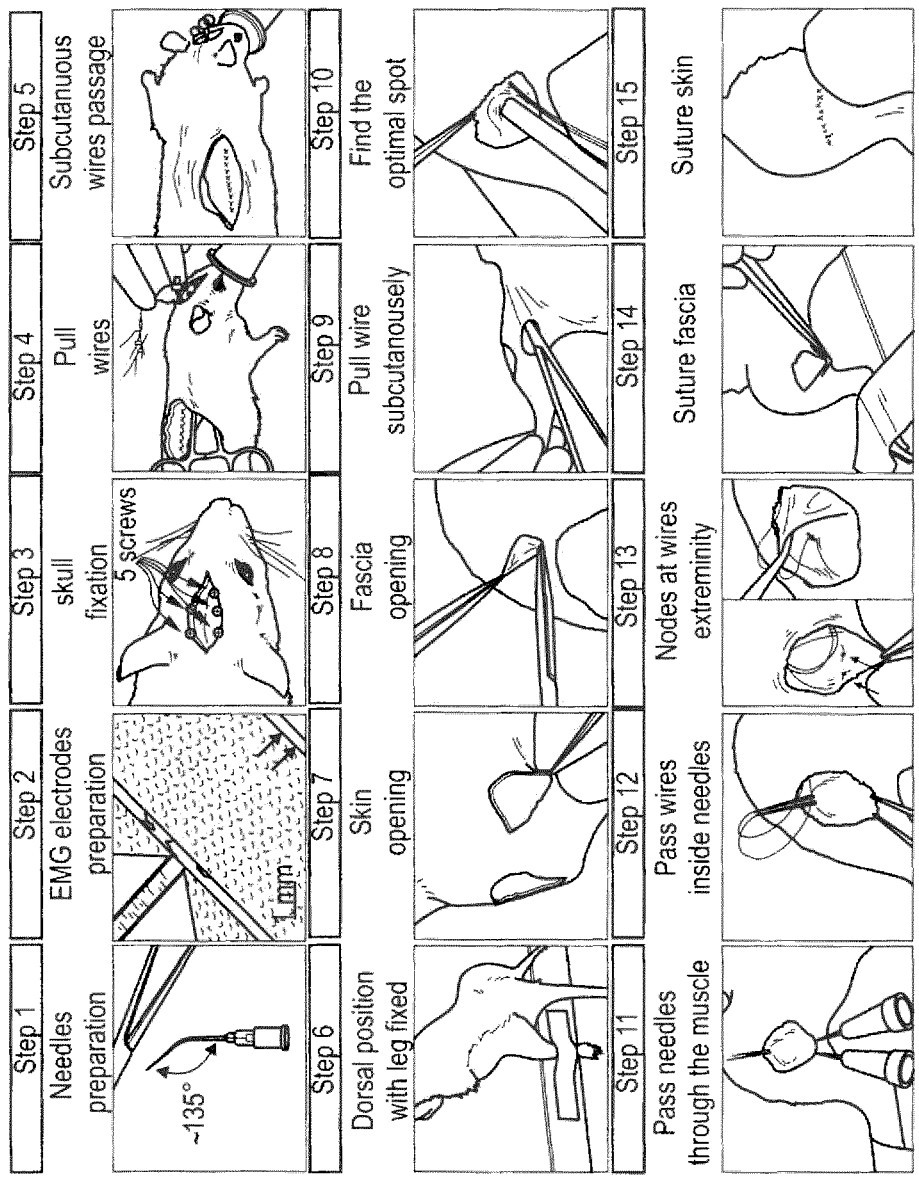
FIG. 4 the implantation procedure of a neuromodulation lead of a system according to FIG. 1, here in connection with the example of the implantation of a neuromodulation lead for a rodent (here a Lewis rat)

FIG. 4 shows the implantation procedure of the neuromodulation lead 22, here in connection with the example of the implantation of a neuromodulation lead for a rodent (here a Lewis rat).

The implantation of a neuromodulation lead for other mammals like monkeys or human beings is similar.

In step ST1 the needles are prepared.

In step ST2 the EMG electrodes are prepared.

In step ST3 a skull fixation is done.

In step ST4 the lead wires are pulled.

In step ST5 subcutaneous wire passage is prepared and provided.

In step ST6 a dorsal position with leg fixed is performed.

In step ST7 a skin opening is performed.

In step ST8 a fascia opening is performed.

In step ST9 the wires are subcutaneously pulled.

In step ST10 the optimal spot is found.

In step ST11 needles are passed through the muscles.

In step ST12 wires are passed inside the needles.

In step ST13 notes at wires extremity are provided.

In step ST14 the fascia is provided with a suture.

In step ST15 a suture to the skin is performed to close the implantation side.

Figure 5:
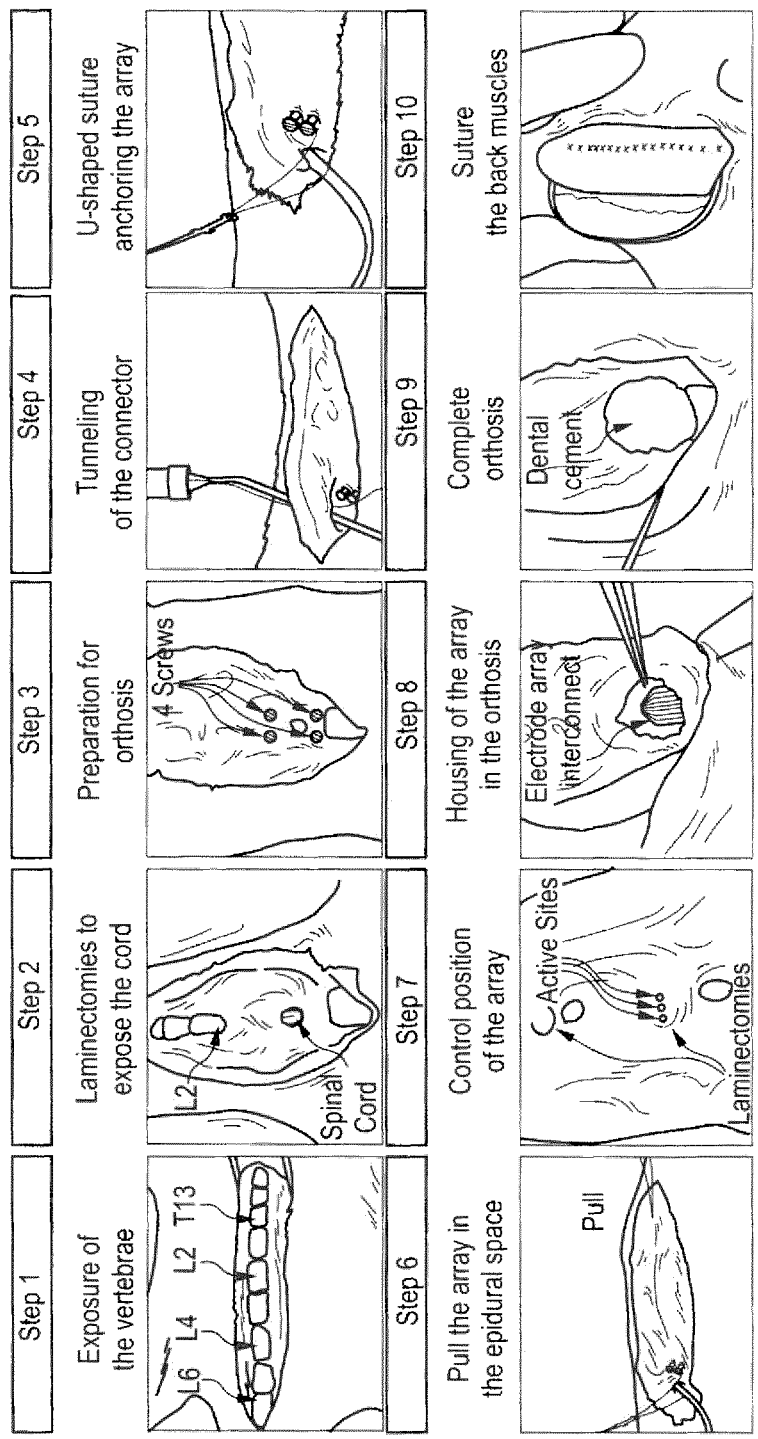
FIG. 5 further steps of implanting an electrode array to the spinal cord.

FIG. 5 shows further steps of implanting an electrode array to the spinal cord.

In step ST100 the exposure of the vertebrae is done.

In step ST110 laminectomies are done to expose the spinal cord.

In step ST120 a preparation for the orthosis is done by using 4 screws.

In step ST140 a tunneling of the connector is prepared and provided.

In step ST150 a ushape suture is provided for anchoring the electrode array of the neuromodulation lead 22.

In step ST160 the array is pulled into the epidural space.

In step ST170 a control position the array is done.

In step ST180 a housing of the array is provided in the orthosis.

In step ST190 a complete orthosis is performed by using dental cement. This orthosis is used for the rodents to support them during "walking". It is not needed for other mammals like primates (e.g. monkeys or humans).

In step ST200 a suture of the back muscles is provided to close the implantation side.

Figure 6A:
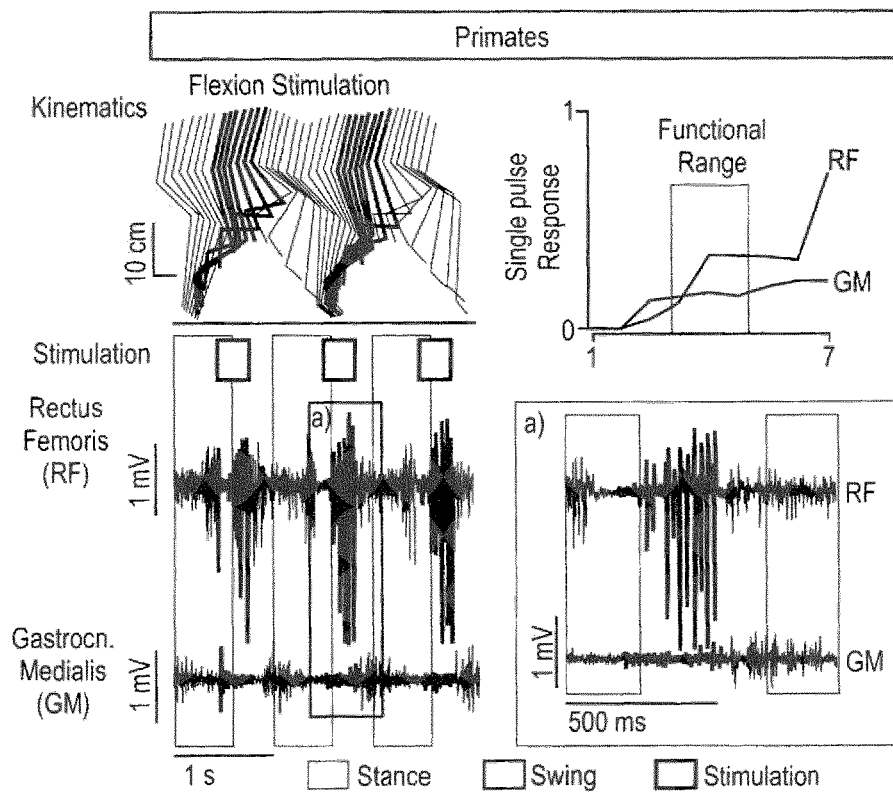
FIG. 6a the kinematics and the stimulation in the functional range on flexion stimulation for primates.
Figure 6B:
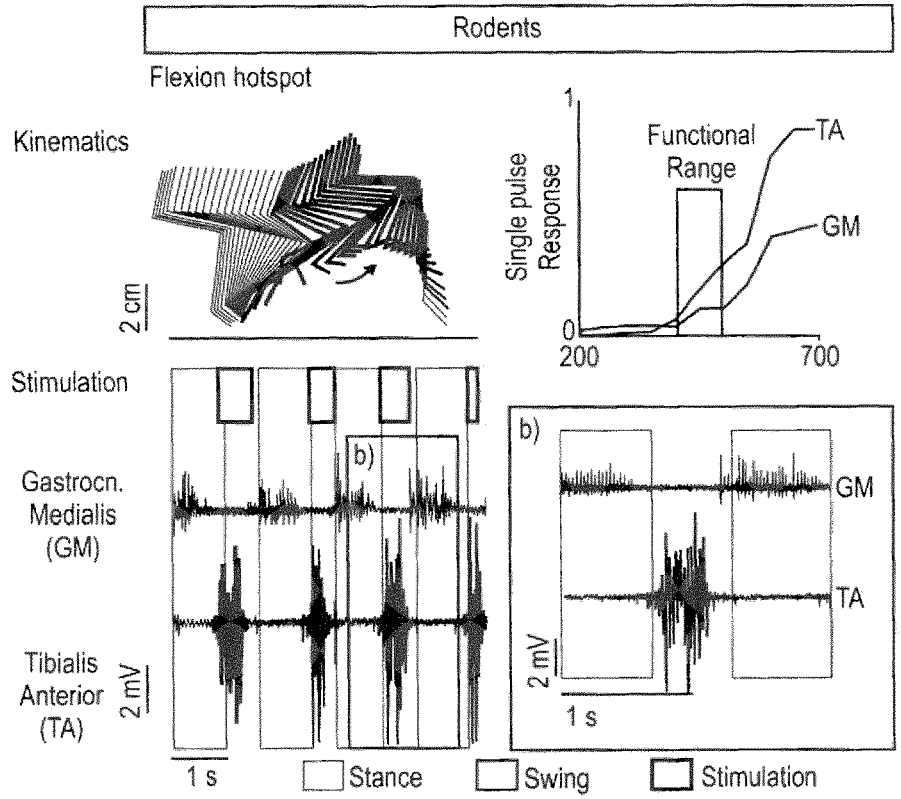
FIG. 6b the kinematics and the stimulation in the functional range on flexion stimulation for rodents.

In FIG. 6a the kinematics and the stimulation in the functional range on flexion stimulation for primates is shown. The corresponding relationship for rodents is shown in FIG. 6b.

Method of Functional Mapping

The method of functional mapping may be performed for example as follows:

Evaluation of the spatial specificity of epidural arrays is achieved by simple electrophysiological testing. A single supra-threshold current pulse of EES, applied through an electrode contact at the lumbosacral level, produces mono- and poly-synaptic electromyographic responses in some leg muscles termed spinal reflexes (FIG. 6a and FIG. 6b).

In particular, the mono-synaptic component of these responses, appearing at the lowest threshold, is related to the direct activation of the Ia afferent fibers. These fibers have excitatory synaptic connections to all the motoneurons of their homonymous muscle. Therefore, given the location of motoneuron pools in the spinal cord (cf. e.g. FIG. 3c and FIG. 3h) and which muscles are activated by single pulses (or low-frequency stimulation, e.g. 0.5-2 Hz) of epidural stimulation, it is possible to infer which roots are stimulated by each of the active sites. This procedure enables to estimate the region of the spinal cord that is preferentially targeted by a specific contact (cf. e.g. FIG. 6a and FIG. 6b).

Indeed, the specificity of epidural arrays for spatiotemporal neuromodulation is not defined by the ability to stimulate single muscles, but rather by the recruitment of specific spinal segments innervating several muscles at the same time. Some antagonist muscles, such as the tibialis anterior and gastrocnemius medialis, may be partially innervated by roots emerging from the same segment. However, spinal circuits and interactions with residual descending control will gate the stimulation effects towards functionally relevant muscles during the execution of a specific movement. The excitability of agonist and antagonist muscles is modulated during gait, resulting in increased functional muscle specificity during movement (cf. e.g. FIG. 6a and FIG. 6b) compared to static measurements. This provides additional robustness in the positioning of the implants. During the implantation procedure, the ability to elicit spinal reflexes in the muscles innervated by the most rostral and the most caudal spinal segments innervating leg muscles (such as the Iliopsoas and Gastrocnemius Medialis respectively) ensures a correct longitudinal placement of the array and a full coverage of the entire lumbosacral spinal cord.

Procedure

Implantation of chronic electromyographic (EMG) electrodes and epidural spinal electrode arrays in rats and primates is done as shown in FIG. 4 and FIG. 5.

For primates or humans the implantation of the neurostimulation lead is done likewise the implantation of electrode arrays for neurostimulation of the spinal cord in connection with pain treatment.

After the implantation, the following exemplary steps for Intra-operative electrophysiology and finalization of the implantation procedure for the epidural array of the neuromodulation lead 22 are performed.

The EMG electrodes are connected and the epidural array to the Real-Time electrophysiology unit.

The system 10 set up to visualize on a monitor and store 50 ms of EMG signals triggered by each stimulation pulse delivered through the epidural array.

Then, the neural stimulator with the neuromodulation pulse generator 24 and the neuromodulation lead 22 is set to current mode (voltage mode can also be used but is not preferred). The stimulation frequency may be chosen at e.g. 0.5 Hz. In general, a current range from 0 to 600 µA in rats and 0 to 5 mA in primates or humans at 200 µs pulse-width may be expected.

After this, one may proceed by stimulating the most rostral sites to verify that the Muscle Evoked Potential of the iliopsoas in response to the epidural stimulation is recruited at lower threshold than the other leg muscles. Stimulation of the most rostral lumbar segments of the spinal cord should induce isolated hip flexion movements associated to each stimulation pulse when the stimulation is applied above motor threshold.

In the next step it is continued by stimulating the most caudal sites to verify that the Muscle Evoked Potential of the Medial Gastrocnemius in both rats and primates (or another most caudally innervated muscle) in response to the epidural stimulation is recruited at lower threshold than other leg muscles. A current amplitude range from e.g. 0 to 300 µA in rats and 0 to 2 mA in primates or humans at 200 µs pulse-width for the stimulation of the caudal spinal cord may be expected. Stimulation of this region should induce isolated ankle dorsi-flexion movements associated to each stimulation pulse when the stimulation is applied above motor threshold.

Then, the longitudinal position of the array may be adjusted by e.g. sliding it under the vertebra and previous steps may be repeated until both conditions are met.

Following to this step/these steps, the medio-lateral positioning of the array is checked by verifying that stimulation of lateral sites at the same spinal level selectively recruits the muscles of the leg ipsilateral to the stimulation site at lower current levels than the muscles of the contralateral leg. The position of the array is adjusted by using the openings provided by the laminectomies at various spinal levels.

Spatial Specificity: Post-Surgical Selection of Optimal Electrode Configurations Firstly, the epidural spinal stimulation system is set up. In rats, the headplug receiving the wires from the epidural electrode array is connected to to a multichannel stimulator controlled by a computer or real-time processor (e.g. RZ2 Bioamp Processor, Tucker-Davis Technologies). In primates or humans establishing communication with an Implantable Pulse Generator (IPG) (e.g. Activa RC, Medtronic). Communication occurs via a telemetry system consisting of an antenna linked to an interface worn by the animal and placed in a custom-made jacket. This interface should be able to transmit information wirelessly (e.g. by Bluetooth) to an external computer. Such systems with real-time communication capabilities do not readily exist as commercial system but can be used as investigational devices through collaborations with biomedical companies such Medtronic.

Optionally, a video recording or motion capture system may be used to record the movements that will be induced by epidural stimulation (as described in the following point).

The spatial selectivity of the electrode array is characterized following a procedure similar to that described on connection with the verification of the Muscle Evoked Potential of muscles of interest. The stimulation is set by selecting an electrode site and send single bipolar electrical pulses (200-µs pulse width) at a frequency of 0.5 Hz. The electrode site being tested is selected as the cathode (negative polarity).

Then, the stimulation amplitude is manually increased from until a motor evoked potential is observed. A motor potential elicited by the stimulation should occur within about 3-8 ms in the rats and 5-15 ms in the primates after the stimulation pulse. Take note of the minimum intensity eliciting a motor potential as the motor threshold.

The intensity is increased until the motor responses on all muscles saturate in amplitude and take note of the saturation amplitude.

A recording of the EMGs is performed while systematically ramping up the stimulation amplitude from 0.9× the motor threshold found until the saturation amplitude found.

The above steps are repeated for each electrode of the spinal implant, until muscle responses evoked by each of the electrode contacts are recorded.

Optionally, a testing of additional multipolar electrode configurations may be performed. In the case in which leg specificity or muscle specificity is considered insufficient, multipolar configurations can be used to increase it. For example if all the electrodes on the left side of the array induce responses in both limbs, multipolar configurations may be tested with the cathode on the left side and the anode on the midline or on the right side in order to steer the activating field towards the desired limb. Likewise, if there is a lack of rostro-caudal selectivity, for example if the iliopsoas (most rostral muscle) is not specifically recruited by the most rostral electrodes, the cathode may be placed on the most rostral electrode and one or several anodes on the electrodes caudal to it.

When all recordings are completed the local procedures defined for awakening and post-sedation care will be performed.

Then, the recruitment curves and the digital characteristic are calculated and computed offline from the data obtained in the steps described above. Recruitment curves indicate the normalized level of activation of each muscle in response to single electrical pulses of increasing amplitude. The EMG activity is normalized by its maximum across all stimulation amplitudes and all stimulation sites. These recorded motor responses can also be translated into spatial maps of motoneuron pool activation, so-called spinal maps. From the recruitment curves, identify a functional range of stimulation amplitudes in which only the muscles activated at the lowest thresholds are significantly recruited. The spinal maps are computed corresponding to this functional range and use them to define the spatial specificity of each electrode configuration.

By analyzing the computed spinal maps, the electrode configuration is determined that creates the highest activation in the spinal segments responsible for flexion of the leg, especially hip flexion (L1-L2 in rats during bipedal locomotion, L1-L2 in primates) and has unilateral responses over a wide range of amplitudes. This configuration is selected to promote global flexion of the leg. Similarly, the electrode configuration is determined that creates the highest activation in the spinal segments responsible for extension of the leg, especially ankle extension (L4-L6 in rats during bipedal locomotion, L6-L7 in primates) and has unilateral responses over a wide range of amplitudes. This configuration is selected to promote global extension of the leg Time Specificity: Determination of stimulation patterns The required timing for each type of stimulation is determined. Prior to the planned experiments, first EMG recordings of a few healthy individuals walking in the same conditions as used for the impaired subjects are performed. From these EMG recordings, the spatiotemporal maps (i.e. digital characteristic maps) of motoneuron activation during healthy locomotion are computed and determined. In rats and primates or humas, the analysis of these spinal maps will reveal that the spinal segments associated with flexion should be activated from the beginning of swing ('foot off') to the middle of swing. Similarly, the spinal segments associated with extension should be activated from the beginning of stance ('foot strike') to the middle of stance.

Then, a system is set up, which is able to detect or predict in real-time the gait events necessary for spatiotemporal neuromodulation: "foot off", "foot strike", "mid-stance", "mid-swing". This system can be based on a real-time motion capture system in case there is residual voluntary motor control and if the animal can wear infrared-reflective markers or other types of motion sensors. Otherwise, the instantaneous motor state can be decoded from neural signals using intracortical microelectrode arrays, electro encephalograms (EEG) or implanted EEG (Ecog).

Following to that, the sequence of stimulation bursts is programmed based on the detected gait events. In case all the detected events are sufficiently separated in time, all of them can be used to trigger the onset or the end of a particular set of stimulation bursts. However, if the stimulator can only accept stimulation commands up to a maximum rate and if the time interval between some consecutive events is too short to send two separate commands, an alternative solution is to pre-program the duration of the stimulation bursts. In this solution, the gait events only trigger the onset of stimulation, and the bursts are terminated automatically after a certain time has elapsed.

In a further step, initial amplitudes and frequencies are selected. To start with this procedure, e.g. one can select a frequency of about 60 Hz for all electrode configurations used in the program defined above. For each electrode configuration, one can select an amplitude around 1.5 times the motor threshold obtained during recruitment curves. Closed-loop spatiotemporal neuromodulation may be tested with this set of parameters. The amplitudes may be adjusted based on kinematics and EMG activity. Each electrode configuration should have a significant effect on the targeted muscle group without loss of muscle specificity.

The stimulation timing may be refined empirically. Alternatively, this can be done automatically with simulation tools or the like.

One may anticipate or delay the onset of each stimulation burst and see if the effect on kinematics and EMG activity is improved. Kinematic effects can be quantified by looking at key variables such as step height or stride length, or by computing an exhaustive list of kinematic variables and using dimensionality reduction techniques such as Principal Component Analysis (PCA). Similarly, one may extend or reduce the duration of each stimulation burst and examine the effect on kinematics and EMG activity. The process may be iterated until an optimal set of parameters is found.

Also, stimulation amplitudes and frequencies may be refined. The timing obtained in the previous step may be used. One may then re-adjust the amplitudes and frequencies. Each electrode configuration should have a significant effect on the targeted muscle group without loss of muscle specificity.

Figure 7:
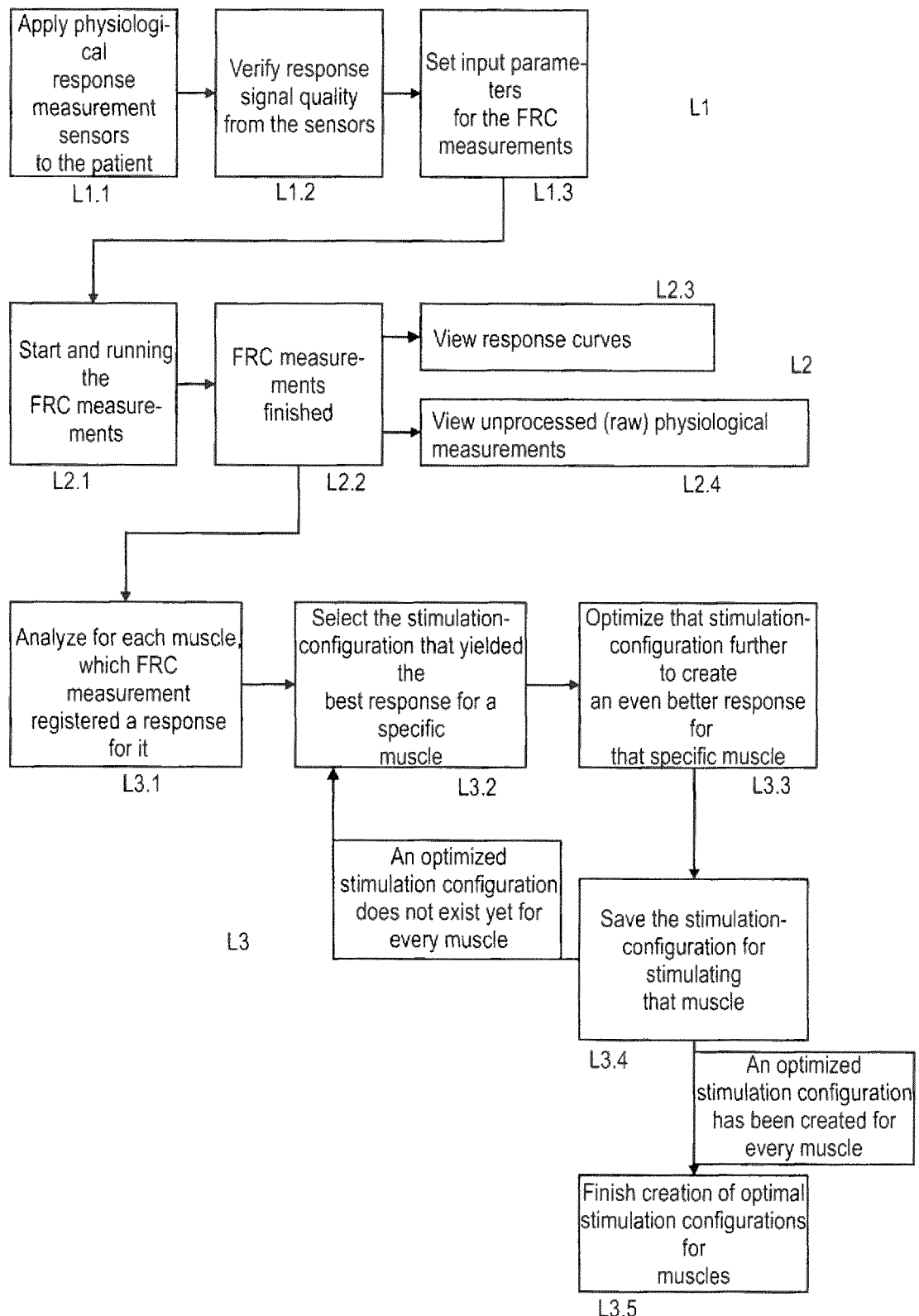
FIG. 7 a workflow for performing the system for planning and/or providing a neuromodulation.

FIG. 7 shows a workflow for performing the system for planning and/or providing a neuromodulation.

In particular, a workflow for performing a postoperative functional recruitment curve measurement for creating a therapy is shown.

Three levels L1, L2 and L3 are shown, wherein level L1 shows the preparation steps, level L2 relates to measuring and reviewing of the functional recruitment curve and level L3 relates to the postoperative use of the functional recruitment curve to create a stimulation for therapy.

Level L1 comprises the steps
"apply physiological response measurement sensors to the patient", i.e. step L1.1,
"verify response signal quality from sensors", i.e. step L1.2,
"set and put parameters for the FRC measurements", i.e. step L1.3.

In other words, in the steps of level L1 all preparation steps will be performed.

In step L1.1 sensors are applied to the patient to measure the physiological response to the stimulation applied.

In step L1.2 this response is taken and then verified in terms of quality.

After that, in step L1.3, the input parameters for the functional recruitment curve measurements are done.

In particular, in level L1 the electrode array for neurostimulation is implanted and may be also checked regarding its positioning.

Steps L1.1, L1.2 and L1.3 may be iteratively performed again and again, in order to position the electrode array correctly.

In level L2 further steps are done for measuring and reviewing the functional recruitment curves.

The steps of level L2 are:
"start and running the FRC measurements", i.e. step L2.1,
"FRC measurements finished", i.e. step L2.2,
"view of response costs", i.e. step L2.3,
"view of unprocessed (raw) physiological measurements", i.e. L2.4.

For measuring and reviewing the recruitment curves as for example shown in FIG. 2, first the start and running of the FRC measurements must be done in step L2.1. For this, specific measurement routines may be available.

After the functional recruitment curve measurements are finished in step L2.2, the response curves (for example as shown in FIG. 2) may be viewed in step L2.3.

Also, it is possible to perform a review of the unprocessed (raw) physiological measurements.

Especially step L2.4 may give hints to the advanced user and help to find out optimal stimulation parameters.

In the steps of level L3, all steps are performed in the postoperative face. Here, the functional recruitment curves are used to create a stimulation for a therapy and to assist the patient in rehabilitation.

In particular, the functional recruitment curves are used to create an epidural electrical stimulation to help the brain help itself, i.e. to re-organize the signal transfer from the brain and spinal cord.

The steps of level L3 comprise the following steps:
"analyze for each muscle, which FRC measurement registered a response for it", i.e. step L3.1,
"select the stimulation-configuration that yielded the best response for a specific muscle", i.e. step L3.2,
"optimize that stimulation-configuration further to create an even better response for that specific muscle", i.e. step L.3.3,
"save the stimulation configuration for stimulating that muscle", i.e. step L3.4,
"finish creation of optimize stimulation configuration for muscles", i.e. step L3.5.

In step L3.1, for each muscle, which is needed for a specific movement, an analysis is performed, which functional recruitment curve might be suitable and comprises a registered response for the intended muscle activity.

In step L3.2 the stimulation configuration is selected that yielded the best response for a specific muscle and that also fits into the context of the sequences or stages for the specific movement.

In step L3.3 this stimulation configuration is optimized to create an even better response for that specific muscle.

Following to that, in step L3.4 the stimulation configuration for stimulating that muscle is saved. If in step L3.4 it is manually, semi automatically or automatically unveiled that an optimized stimulation configuration does not exist yet for every muscle, then it is returned to step L3.2 and then continued with step L3.3 and L3.4 again.

In case that an optimized stimulation configuration has been created for every muscle, in step L3.5 the creation of optimal stimulation configuration for muscles will be finished.

As mentioned above, the system 10 comprises a neuromodulation setting stimulation module, which is configured and arranged to translate the digital characteristic . . . neuromodule parameter settings for a neuromodulation treatment of a subject. Also, there is a stimulation input module which provides an enabled . . . control by inputting stimulation related response data via the stimulation related response data input module.

Figure 8:
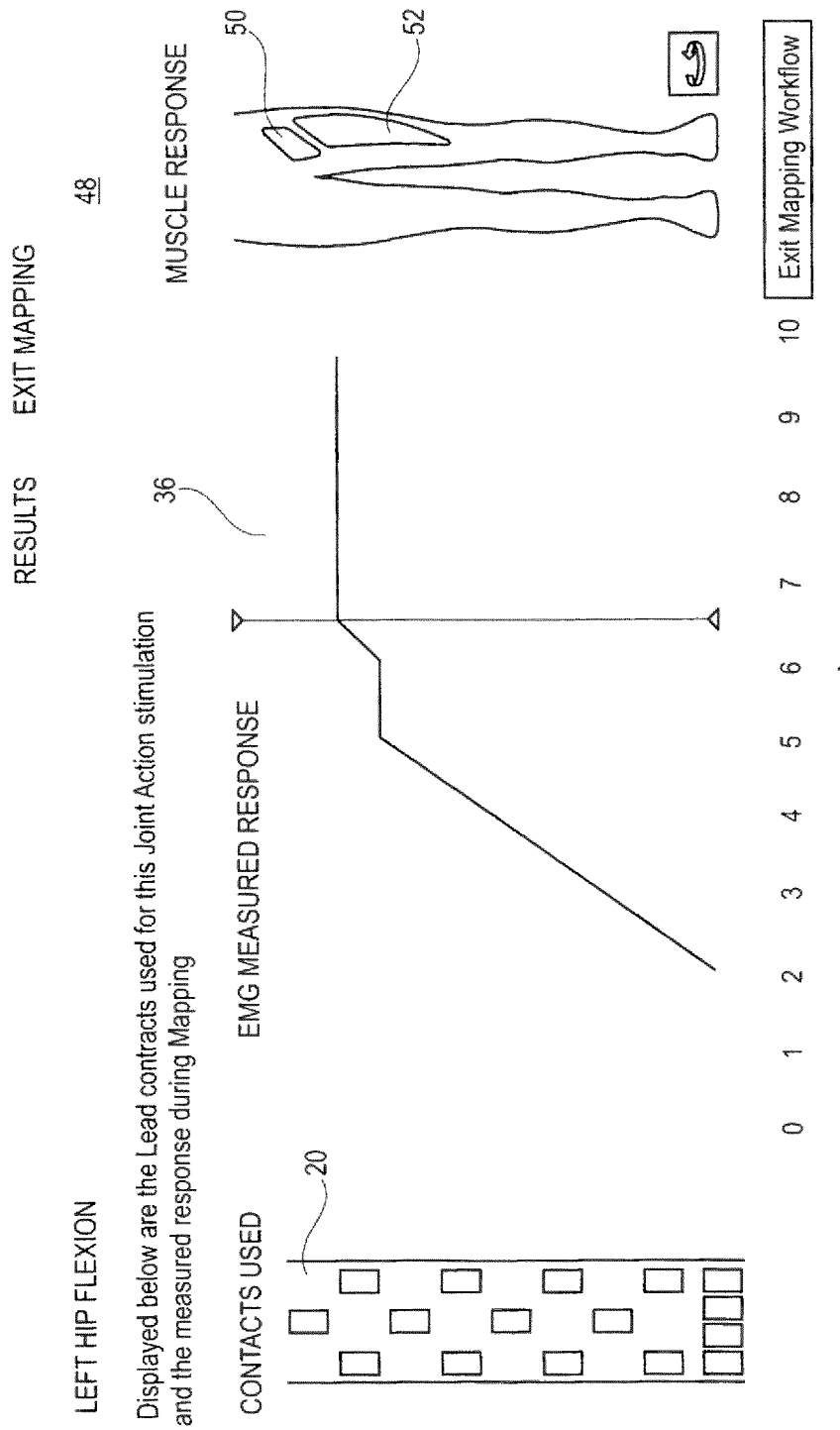
FIG. 8 an example of a stimulation related response data input module.

FIG. 8 shows an example of such a stimulation related response data input module 48, which can be displayed by means of the visualization module 20.

The visualization module 20 may be in such an embodiment a tablet PC.

FIG. 8 is here an overview of the digital characteristic map as shown for example also in FIG. 2. The input module 48 also has an input section—here input sections 50 and 52—for the representation of the muscles to be stimulated.

By tipping/activating the input section 50, the iliopsoas muscle may be stimulated and the respective stimulation parameters may be selected inversely.

Similarly, by tipping/activating the input section 52, the respective stimulation parameters for stimulating the right femoris may be selected.

In the left section a representation of the neuromodulation lead 20 is shown and the respective electrodes of the stimulation lead, that are activated for stimulating the respective muscles as shown in the right section are also indicated.

Similar mappings may be also shown and established for other muscles and other movements.

Here, the movement is "left hip flexion".

Note that the example control and estimation routines included herein can be used with various neuromodulation and/or neurostimulation system configurations. The control methods and routines disclosed herein may be stored as executable instructions in non-transitory memory and may be carried out by the control unit in combination with the various sensors, actuators, and other system hardware in connection with a medical neurostimulation system. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the control unit, where the described actions are carried out by executing the instructions in a system including the various hardware components in combination with a electronic control unit.

Explicitly disclosed in connection with the above disclosure is the following aspect:
1. A method for planning and/or providing neuromodulation, including neurostimulation, comprising
   linking and/or translating stimulation related basic data into and/or with response data and/or artificial response data to generate transfer data, the transfer data comprising link data and/or translation data and/or artificial response data,
   generating a digital characteristic map based on stimulation related basic data and stimulation related response data and the transfer data, the digital characteristic map describing an interrelation between the stimulation related basic data and the stimulation related response data and the transfer data; and automatically analyzing the digital characteristic map to generate.
2. The method according to aspect 1, wherein the method further comprises applying machine learning to generate the characteristic map.

REFERENCES 10 neuromodulation and/or neuro stimulation system
12 physiological response measurement sensor
14 physiological response measurement receiver and processor
16 computer
18 software
20 visualization module
22 neuromodulation lead
24 neuromodulation pulse generator
26 first data input module
28 stimulation related basic data storage module
30 second data input module
32 stimulation related response data storage module
34 transfer module
36 digital characteristic map
38 mapping module
40 virtual mapping module
42 correlation and/or simulation module, analysis module
44 neuromodulation settings generation module
46 transfer interface
48 stimulation related response data input module
50 input section
52 input section
M1 first muscle
M2 second muscle
P patient
P1 onset point
P2 saturation point
P3 specificity point
P1' onset point
P2' saturation point
S storage

The invention claimed is:
1. A system for planning and/or providing neuromodulation, especially neurostimulation, comprising:
   a stimulation related basic data storage module for storing stimulation related basic data, wherein the stimulation related basic data comprise stimulation descriptions, and are received via a first data input module,
   a stimulation related response data storage module for storing stimulation related response data, wherein the stimulation related response data comprise results triggered and received as response to the neuromodulation, and are obtained via a second data input module,
   a transfer module configured and arranged such that the stimulation related basic data received by the first data input module are linked with and/or translated into the stimulation related response data and/or artificial response data created by the transfer module, wherein data generated by the transfer module are transfer data, the transfer data comprising data filling gaps where there is no direct link between stimulation related basic data and stimulation related response data,
   a transfer response data storage module for storing the transfer data, a mapping module configured and arranged such that, based on the stimulation related basic data, the stimulation related response data, and the transfer data, a digital characteristic map is generated, which describes an interrelation between the stimulation related basic data, the stimulation related response data, and the transfer data, and an analysis module configured and arranged such that the digital characteristic map is analyzed automatically.

2. The system according to claim 1, wherein the analysis module is configured and arranged such that onset points within the digital characteristic map are identified automatically.

3. The system according to claim 1, wherein the analysis module is configured and arranged such that saturation points within the digital characteristic map are identified automatically.

4. The system according to claim 1, wherein the analysis module is configured and arranged such that specificity points within the digital characteristic map are identified automatically.

5. The system according to claim 1, further comprising a visualization module.

6. The system according to claim 5, wherein the visualization module is configured and arranged such that at least partially stimulation related basic data and at least partially stimulation related response data are displayed.

7. The system according to claim 5, wherein the visualization module is configured and arranged such that stimulation related response data are visualized at least schematically with representations of muscles or muscles group receiving neuro stimulation.

8. The system according to claim 1, further comprising a stimulation related response data input module, wherein the system is configured and arranged such that an inverse control is provided by inputting the stimulation related response data via the stimulation related response data input module, and the system further comprising a selection module, which is configured and arranged such that, based on the digital characteristic map, suitable stimulation related basic data are selected.

9. The system according to claim 1, further comprising a neuromodulation settings generation module, which is configured and arranged to translate the digital characteristic map into neuromodulation parameter settings for a neuromodulation treatment of a subject.

10. The system according to claim 9, wherein the neuromodulation settings generation module comprises a transfer interface, which is configured and arranged for transferring neuromodulation parameter settings to a neuromodulation device.

11. A method for planning and/or providing neuromodulation, including neurostimulation, comprising:

linking and/or translating stimulation related basic data into and/or with response data and/or artificial response data to generate transfer data, the transfer data comprising link data and/or translation data and/or artificial response data;

generating a digital characteristic map based on stimulation related basic data comprising stimulation descriptions, and stimulation related response data, wherein the stimulation related response data comprise results triggered and received as response to the neuromodulation, and the transfer data, wherein the digital characteristic map describes an interrelation between the stimulation related basic data, the stimulation related response data, and the transfer data; and automatically analyzing the digital characteristic map to identify one or more of onset points, specificity points, and saturation points within the digital characteristic map.

12. The system of claim 1, wherein the stimulation descriptions comprise stimulation type, stimulation element, and stimulation characteristics.

\* \* \* \* \*